United States Patent
Arnold et al.

(10) Patent No.: US 11,896,231 B2
(45) Date of Patent: Feb. 13, 2024

(54) COUPLING FEATURE FOR CIRCULAR SURGICAL STAPLER END EFFECTOR

(71) Applicant: Cilag GmbH International, Zug (CH)

(72) Inventors: Bradley A. Arnold, Mason, OH (US); Dylan Rushton, Novi, MI (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/471,631

(22) Filed: Sep. 10, 2021

(65) Prior Publication Data

US 2023/0084824 A1    Mar. 16, 2023

(51) Int. Cl.
*A61B 17/064*    (2006.01)
*A61B 17/115*    (2006.01)
*A61B 17/00*    (2006.01)

(52) U.S. Cl.
CPC . *A61B 17/1155* (2013.01); *A61B 2017/00477* (2013.01)

(58) Field of Classification Search
CPC ...... A61B 17/1155; A61B 2017/00473; A61B 2017/00477
See application file for complete search history.

(56) References Cited

U.S. PATENT DOCUMENTS

| | | | |
|---|---|---|---|
| 9,980,730 B2 | 5/2018 | Sgroi | |
| 10,646,222 B2 | 5/2020 | Penna et al. | |
| 2015/0108201 A1* | 4/2015 | Williams | A61B 17/1155 227/177.1 |
| 2015/0320420 A1* | 11/2015 | Penna | A61B 17/072 227/176.1 |
| 2016/0157856 A1* | 6/2016 | Williams | A61B 17/068 227/175.1 |
| 2016/0192934 A1* | 7/2016 | Williams | A61B 17/068 29/451 |
| 2016/0192938 A1* | 7/2016 | Sgroi, Jr. | A61B 17/1155 227/175.1 |
| 2016/0310141 A1* | 10/2016 | Penna | A61B 17/1155 |
| 2019/0261993 A1* | 8/2019 | Prior | A61B 17/064 |
| 2020/0229815 A1* | 7/2020 | Penna | A61B 17/072 |

OTHER PUBLICATIONS

International Search Report and Written Opinion dated Dec. 13, 2022 for Application No. PCT/IB2022/058391, 13 pgs.

* cited by examiner

*Primary Examiner* — Eyamindae C Jallow
(74) *Attorney, Agent, or Firm* — Frost Brown Todd LLP

(57) ABSTRACT

A surgical stapling instrument includes a body member having a distal end. The distal end is configured to be fixedly secured to an annular deck member having a plurality of staple openings. The body member is configured to slidably house a staple driver member. The body member includes a radially expandable collar having at least one latching feature. The surgical stapling instrument also includes a shaft assembly, including a proximal sheath portion, a distal sheath portion, and at least one protrusion extending radially outwardly from the distal sheath portion. The at least one protrusion includes at least one abutment surface configured to engage the at least one latching feature of the radially expandable collar for coupling the body member to the shaft assembly.

20 Claims, 23 Drawing Sheets

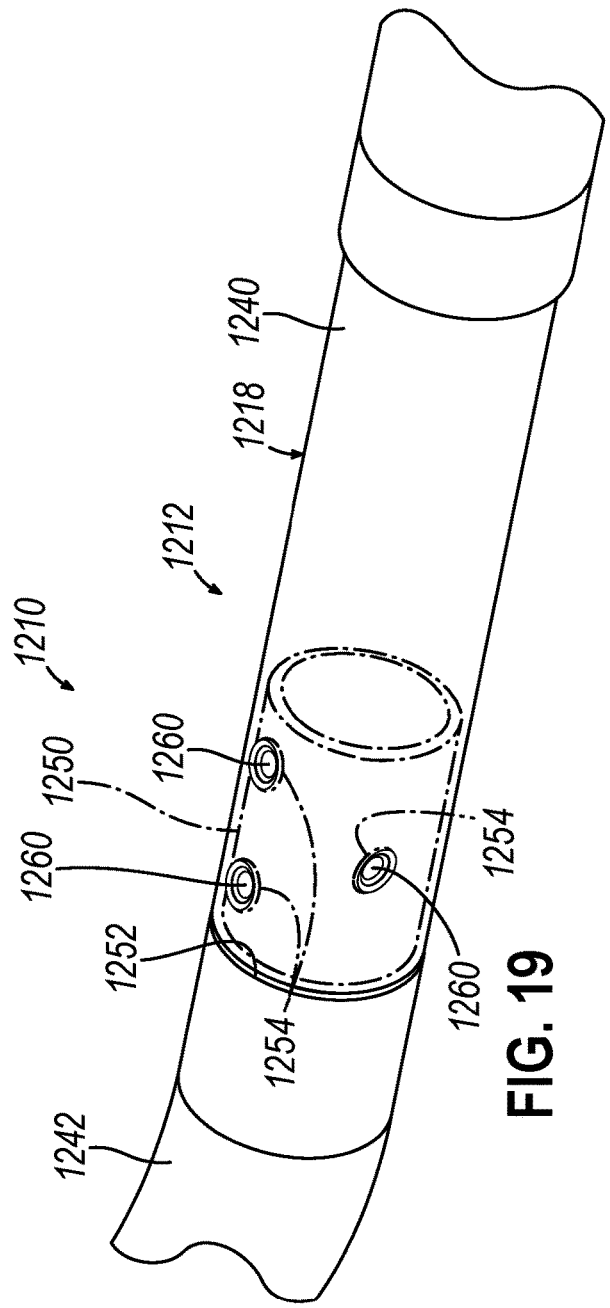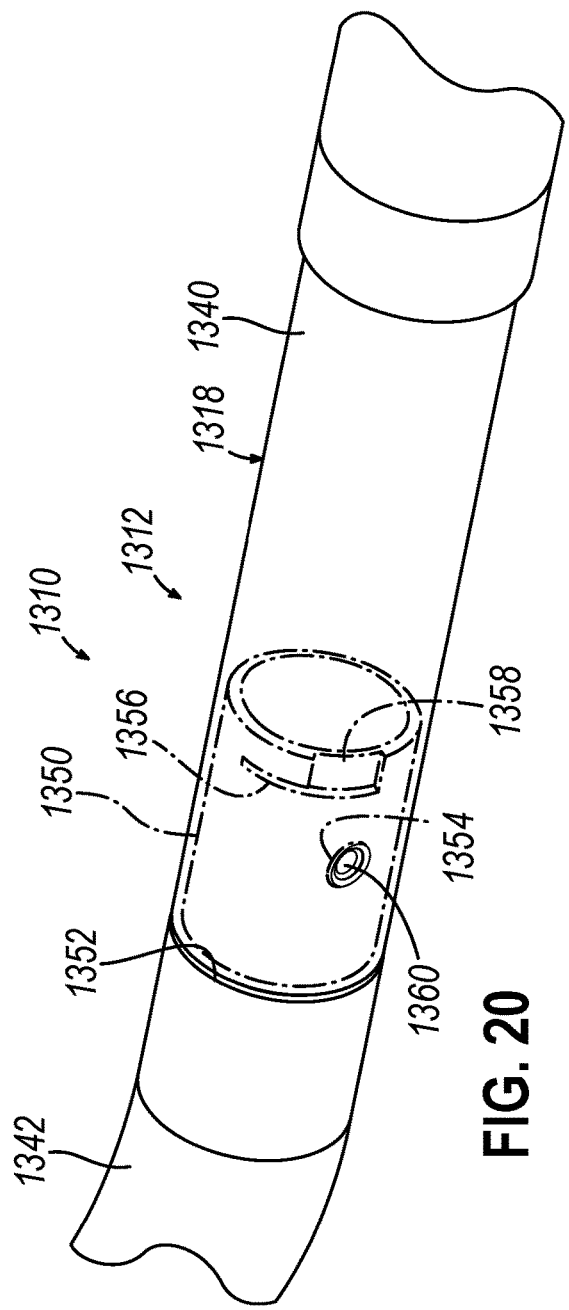

COUPLING FEATURE FOR CIRCULAR SURGICAL STAPLER END EFFECTOR

BACKGROUND

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018now abandoned; and U.S. Pat. No. 10,709,452, entitled "Methods and Systems for Performing Circular Stapling," issued Jul. 14, 2020. The disclosure of each of the above-cited U.S. patenttent Publications and U.S. patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 19 depicts a partial perspective view of another exemplary circular surgical stapler that includes a shaft assembly having a straight portion and a curved portion, showing a rigid collar of the curved portion having a plurality of bores configured to receive corresponding crimp detents of the straight portion;

FIG. 20 depicts a partial perspective view of another exemplary circular surgical stapler that includes a shaft assembly having a straight portion and a curved portion, showing a rigid collar of the curved portion having a plurality of bores configured to receive corresponding crimp detents of the straight portion, and further showing the rigid collar having a semi-annular groove and proximal recessed entryway for receiving a rib of the straight portion to provide a bayonet coupling between the straight and curved portions;

Figure 1:
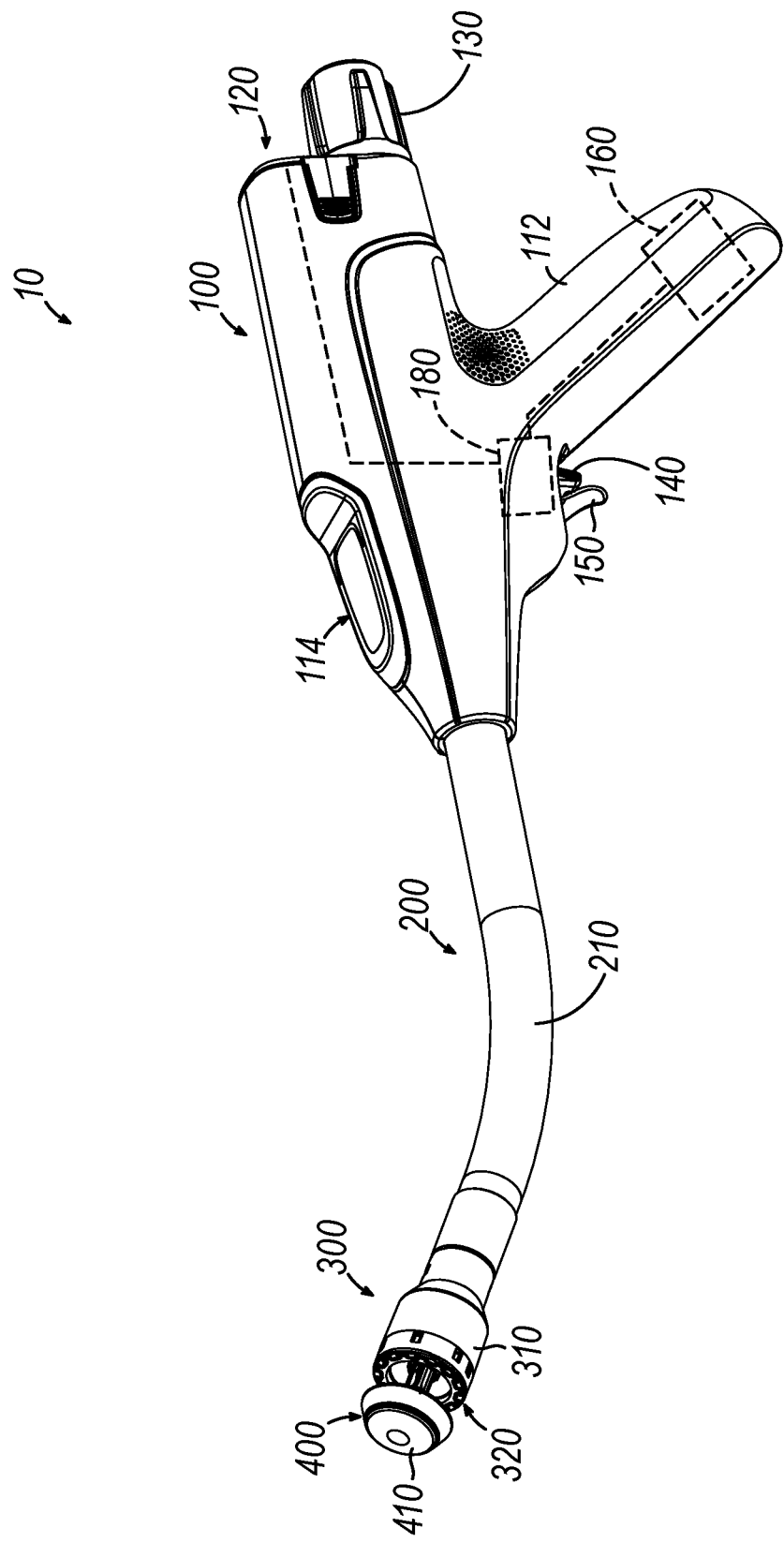
FIG. 1 depicts a perspective view of an exemplary circular surgical stapler that includes a handle assembly, a shaft assembly, and an end effector having a stapling head assembly and an anvil.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," "clockwise," "counterclockwise," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Overview of Exemplary Circular Surgical Stapling Instrument

Figure 2:
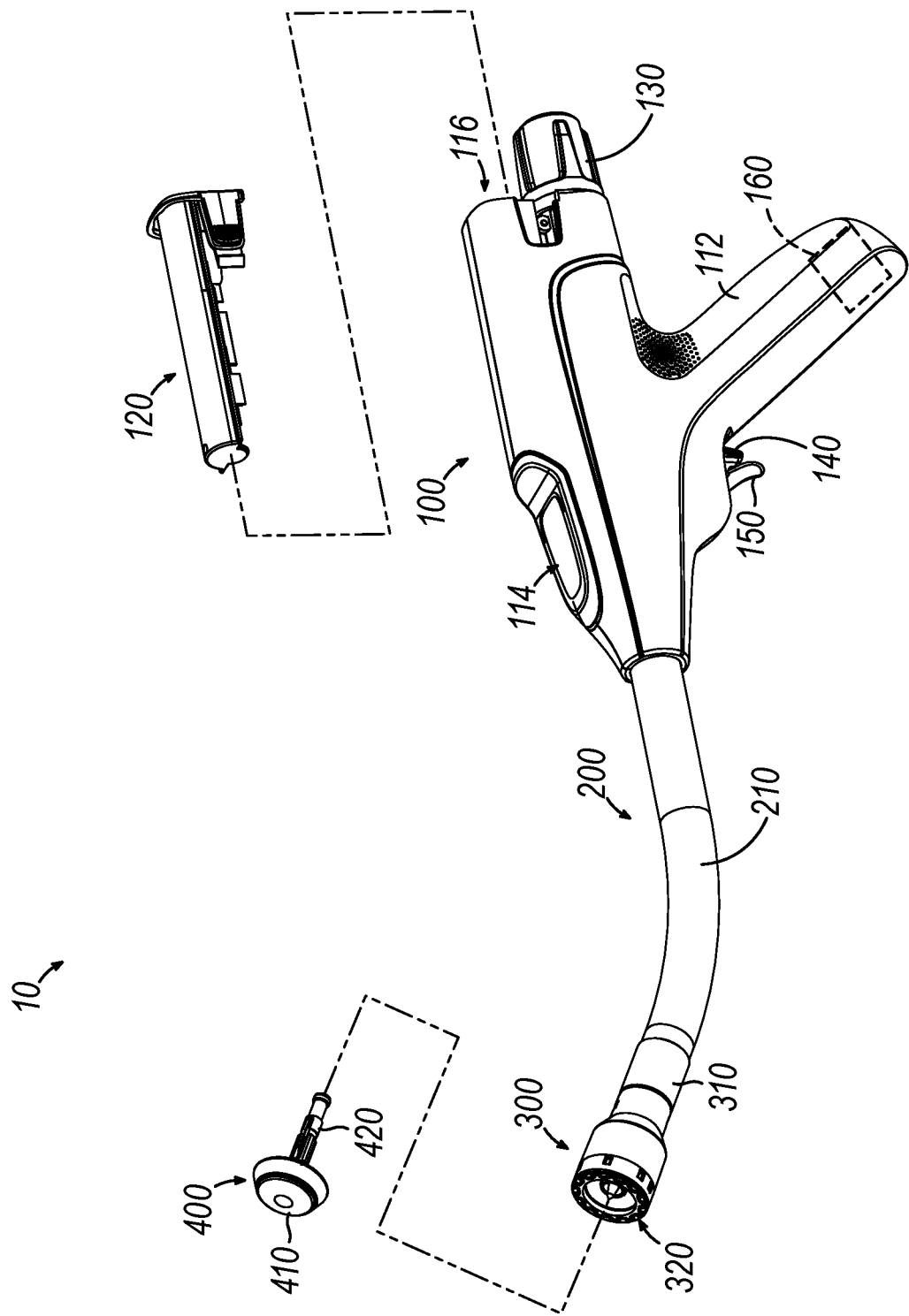
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
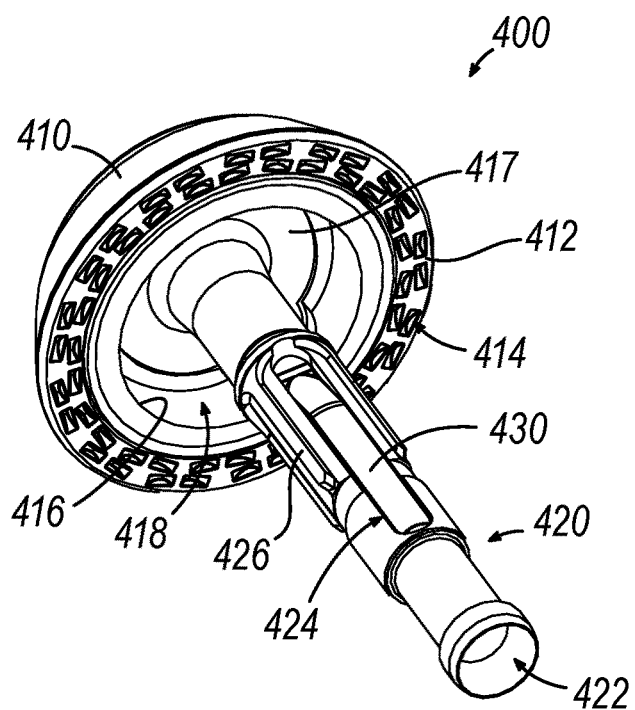
FIG. 3 depicts a perspective view of the anvil of the circular stapler of FIG. 1.

As best seen in FIG. 3, anvil (400) of the present example comprises a head (410) and a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418) and is configured to provide the operator with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members.

B. Exemplary Stapling Head Assembly

Figure 4:
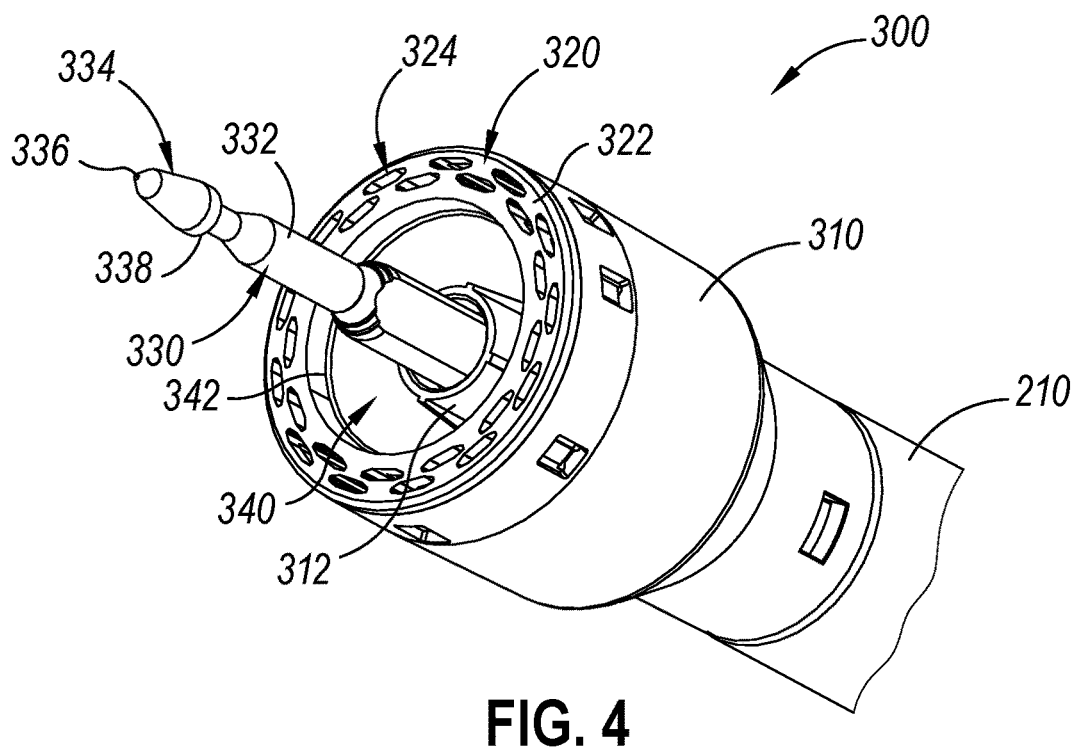
FIG. 4 depicts a perspective view of the stapling head assembly of the circular stapler of FIG. 1.
Figure 5:
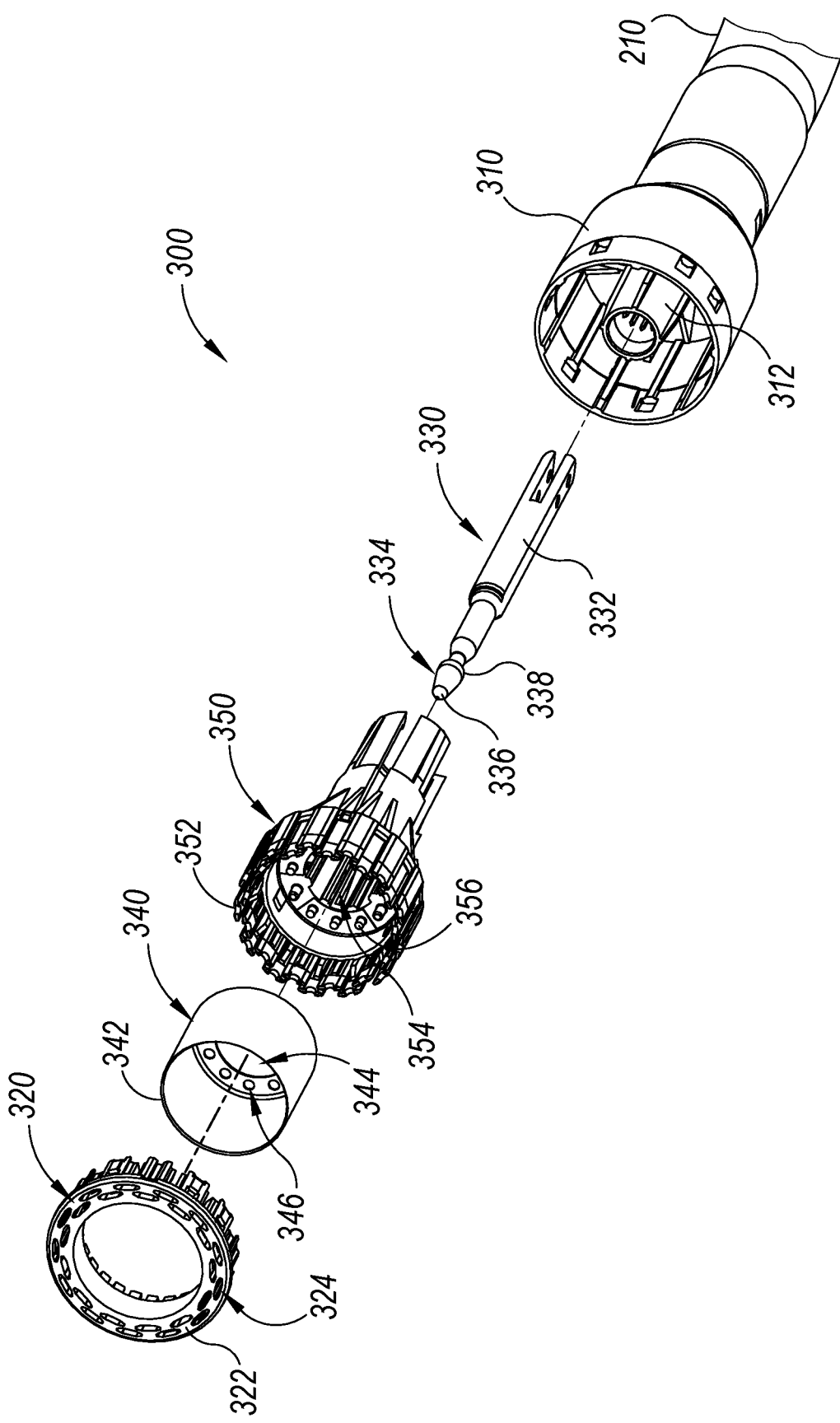
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal surface (338). Head (334) and the distal portion of shaft (332) are configured for insertion into bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As shown best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of the inner annular array of staple drivers (352). Knife member (340) also defines a central opening that is configured to coaxially receive core member (312) of body member (310). An annular array of openings (346) formed in knife member (340) is configured to mate with the annular array of studs (356) of staple driver member (350), such that knife member (340) is fixedly secured to staple driver member (350) via studs (356) and openings (346).

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 4, deck member (320) has a central opening that defines an inner diameter that is just slightly larger than the outer diameter defined by knife member (340). Deck member (320) is thus configured to permit knife member (340) to translate longitudinally through the central opening concurrently with longitudinal translation of staple driver member (350). In particular, knife member (340) is configured to actuate relative to deck member (340) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
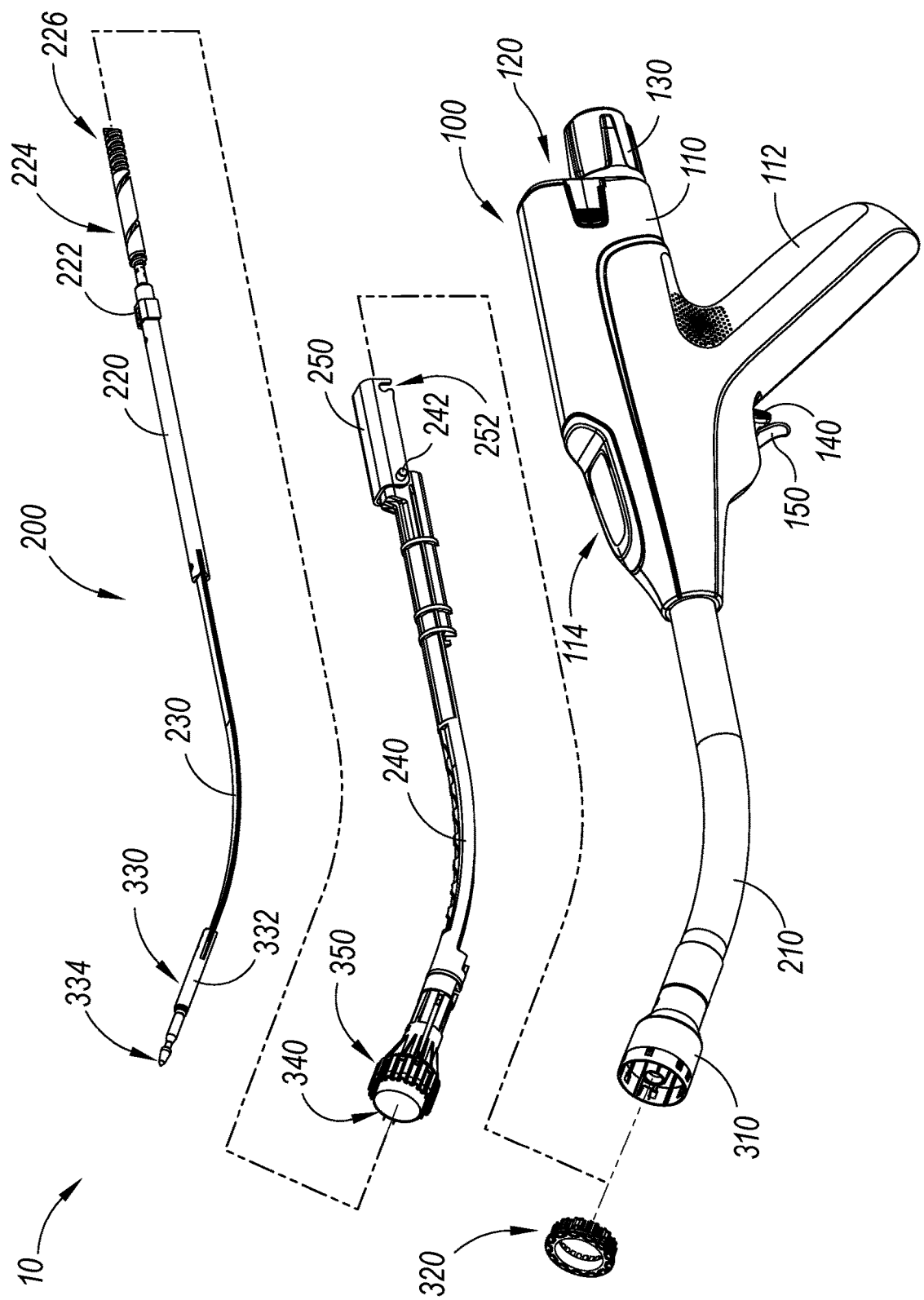
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to the proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extend anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating the switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

Figure 7A:
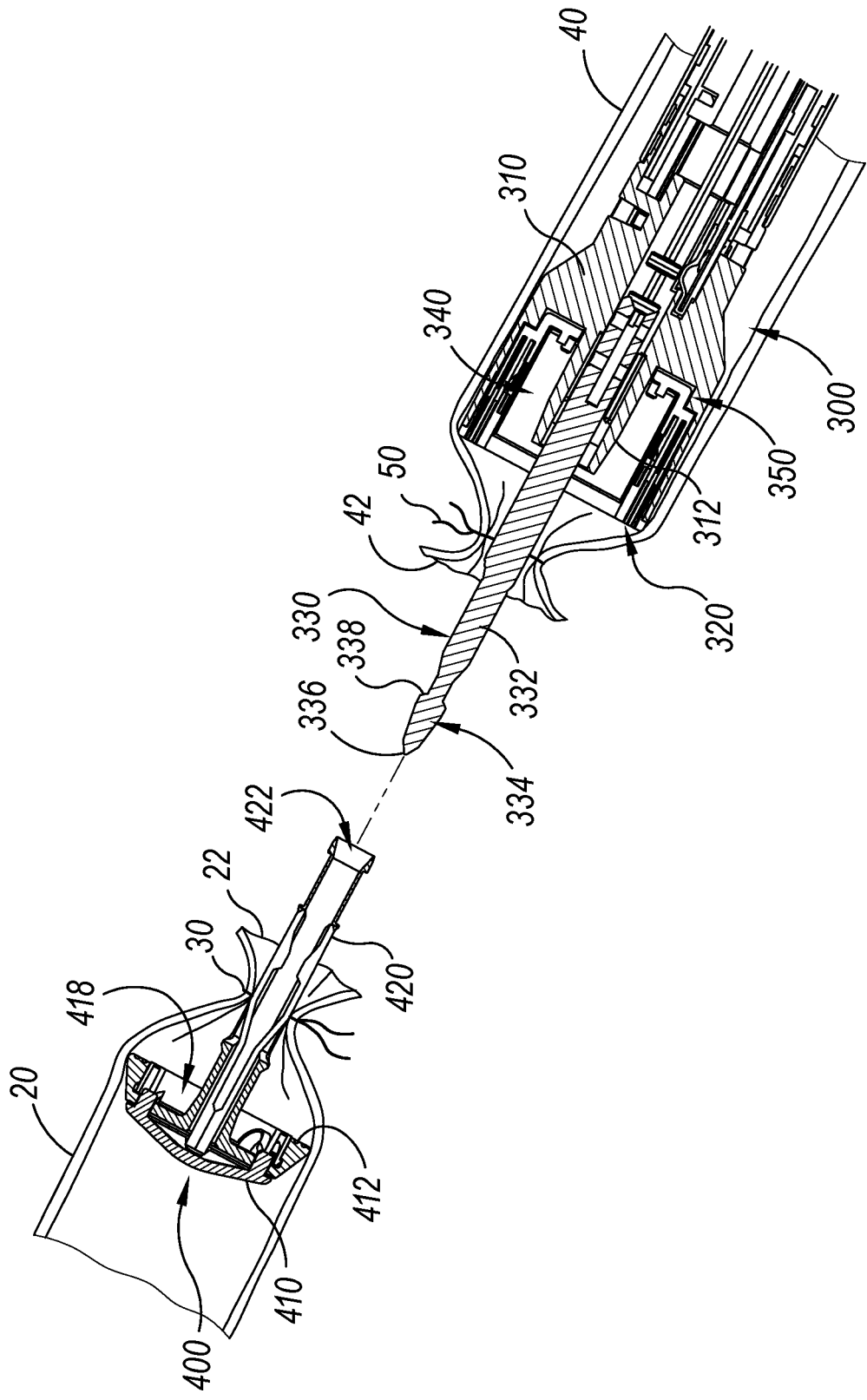
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50)

is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
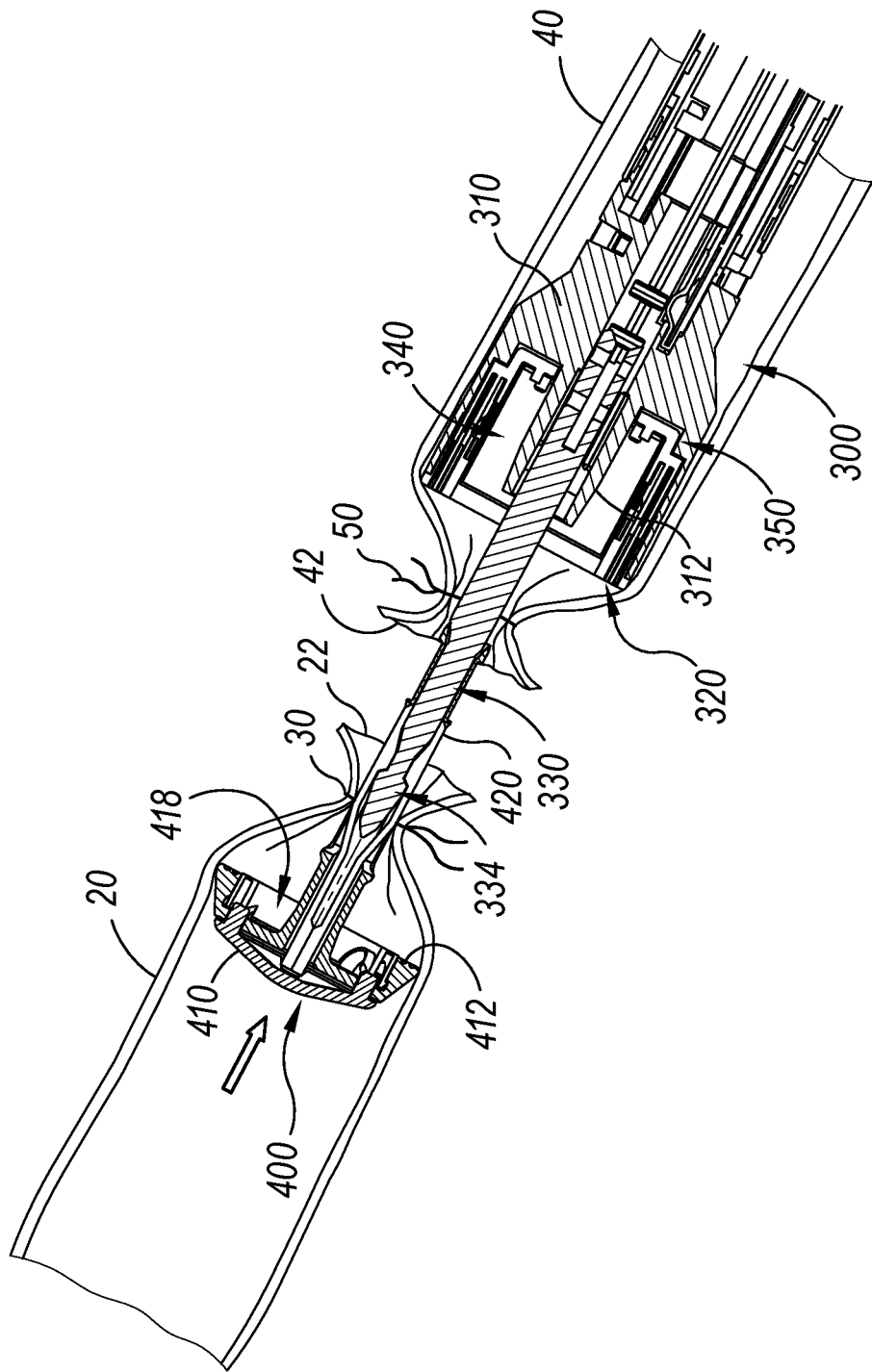
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
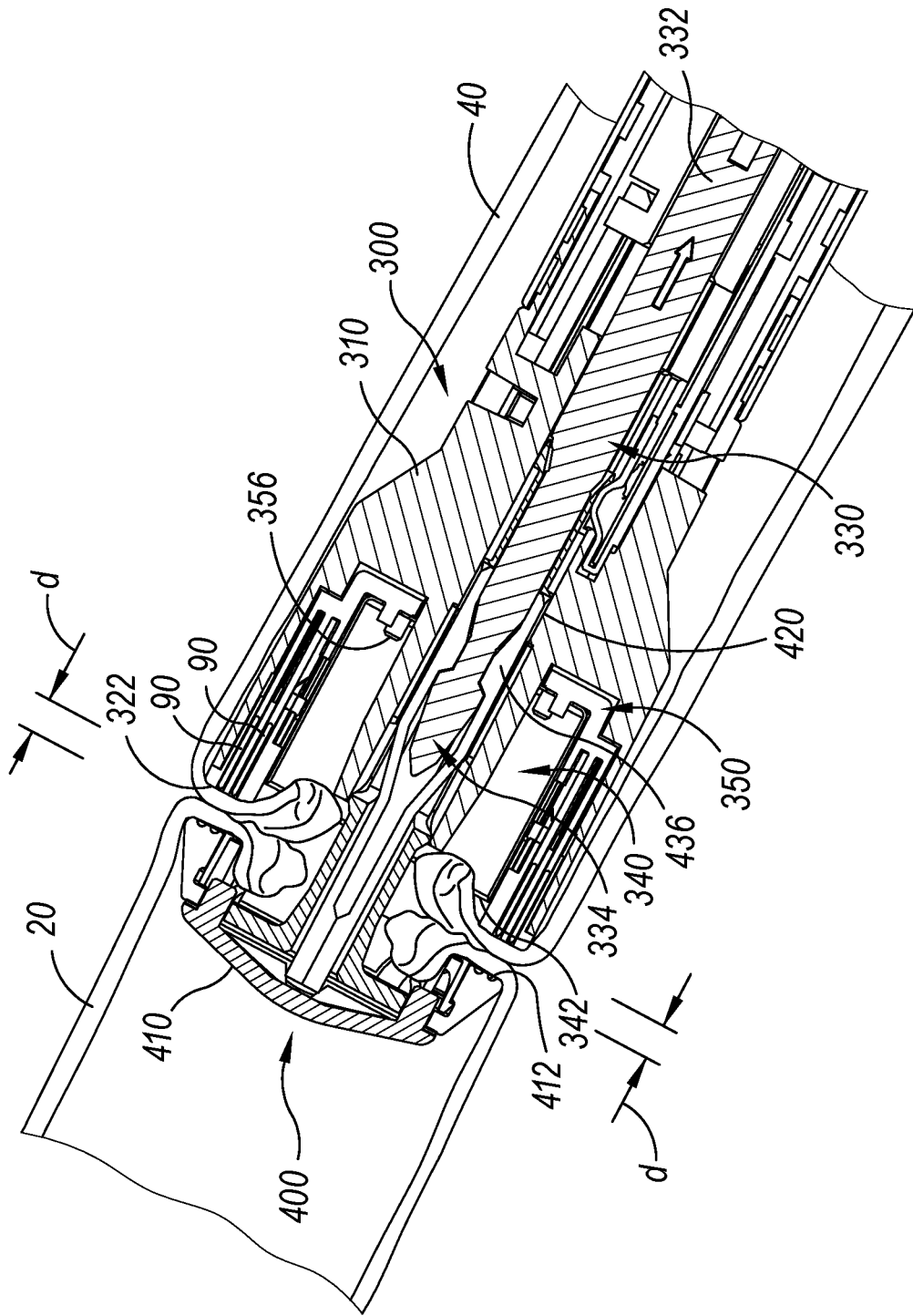
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (not shown) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and the interior of knife member (340). Additionally, washer (417) positioned within annular recess (418) of anvil (400) is broken by knife member (340) when the knife member (340) completes a full distal range of motion from the position shown in FIG. 7C to the position shown in FIG. 7D. It should be understood that washer (417) may also serve as a cutting board for knife member (340) to assist in cutting of tissue.

Figure 7D:
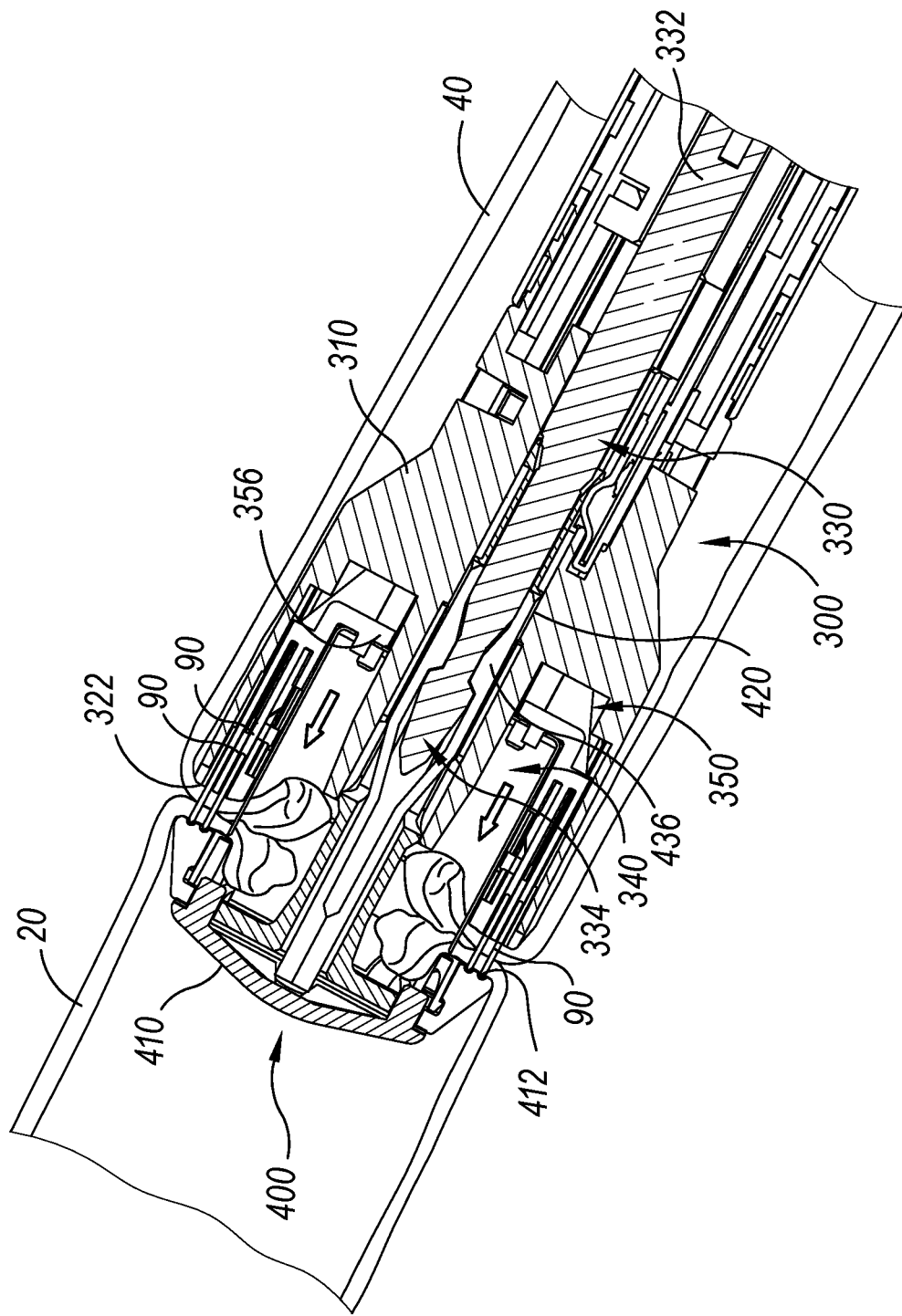
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
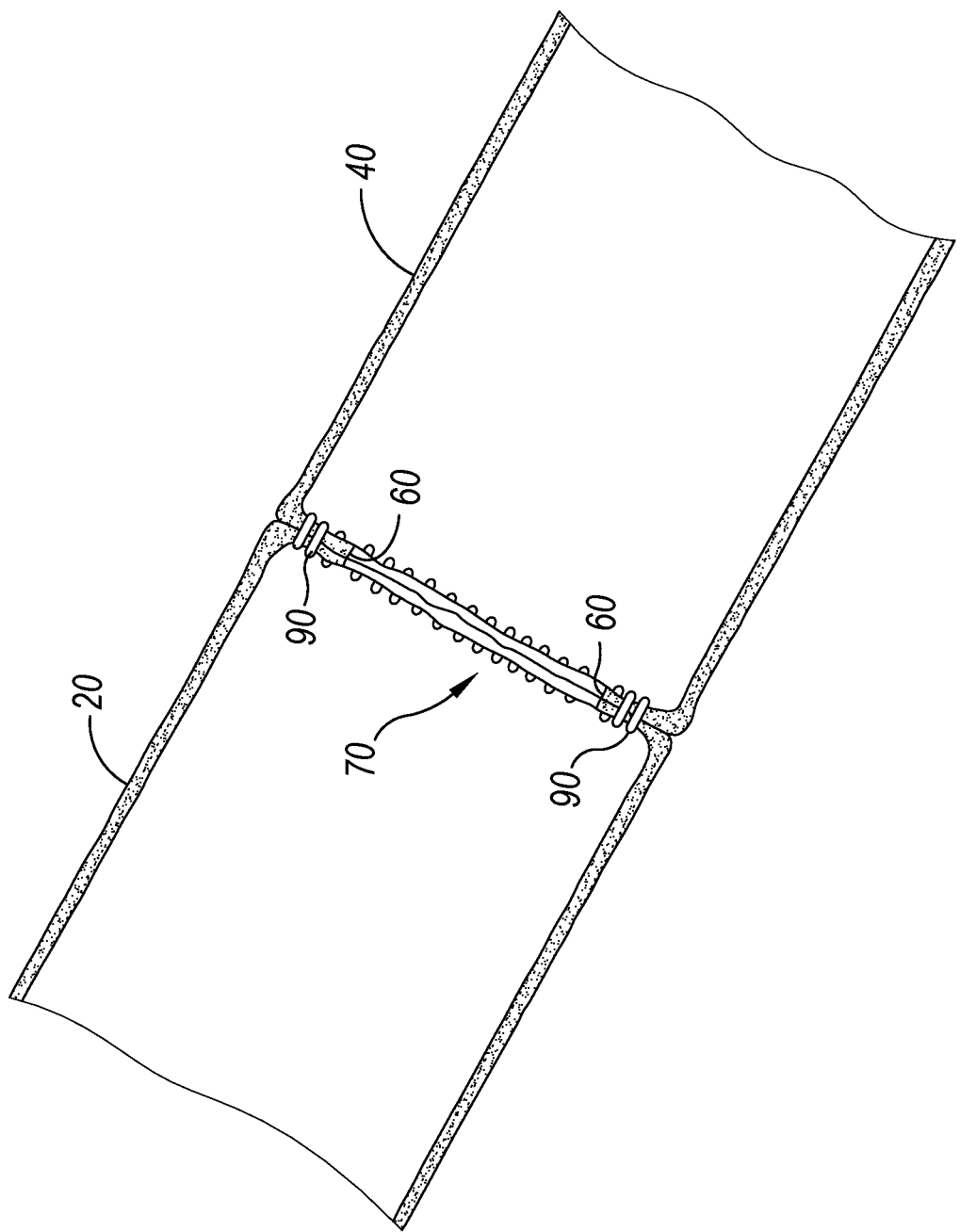
FIG. 7E depicts a cross-sectional side view of the first and second sections of the digestive tract of FIG. 7A joined together at an end-to-end anastomosis formed with the circular stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Exemplary Features for Coupling Stapling Head Assembly to Shaft Assembly

As described above, stapling head assembly (300) is coupled to a distal end of shaft assembly (200). More particularly, body member (310) of stapling head assembly (300) is fixedly secured to outer sheath (210) of shaft assembly (200). It will be appreciated that body member (310) may be fixedly secured to outer sheath (210) via any suitable coupling technique to inhibit relative rotational and axial movement between body member (310) and outer sheath (210) and thereby inhibit inadvertent malfunctioning and/or detachment of stapling head assembly (300) from shaft assembly (200). For example, body member (310) may be fixedly secured to outer sheath (210) via magneforming (also referred to as "electromagnetic forming" or "EM forming"), such as by inducing a current in outer sheath (210) using pulsed electromagnetic fields to thereby reshape a distal end of outer sheath (210) into secure engagement with body member (310). In some instances, it may be desirable to fixedly secure body member (310) to outer sheath (210) via a different coupling technique other than magneforming, such as to reduce or eliminate the need for pulsed electromagnetic fields, for example. Each of the coupling features described below provides such functionality.

Figure 8:
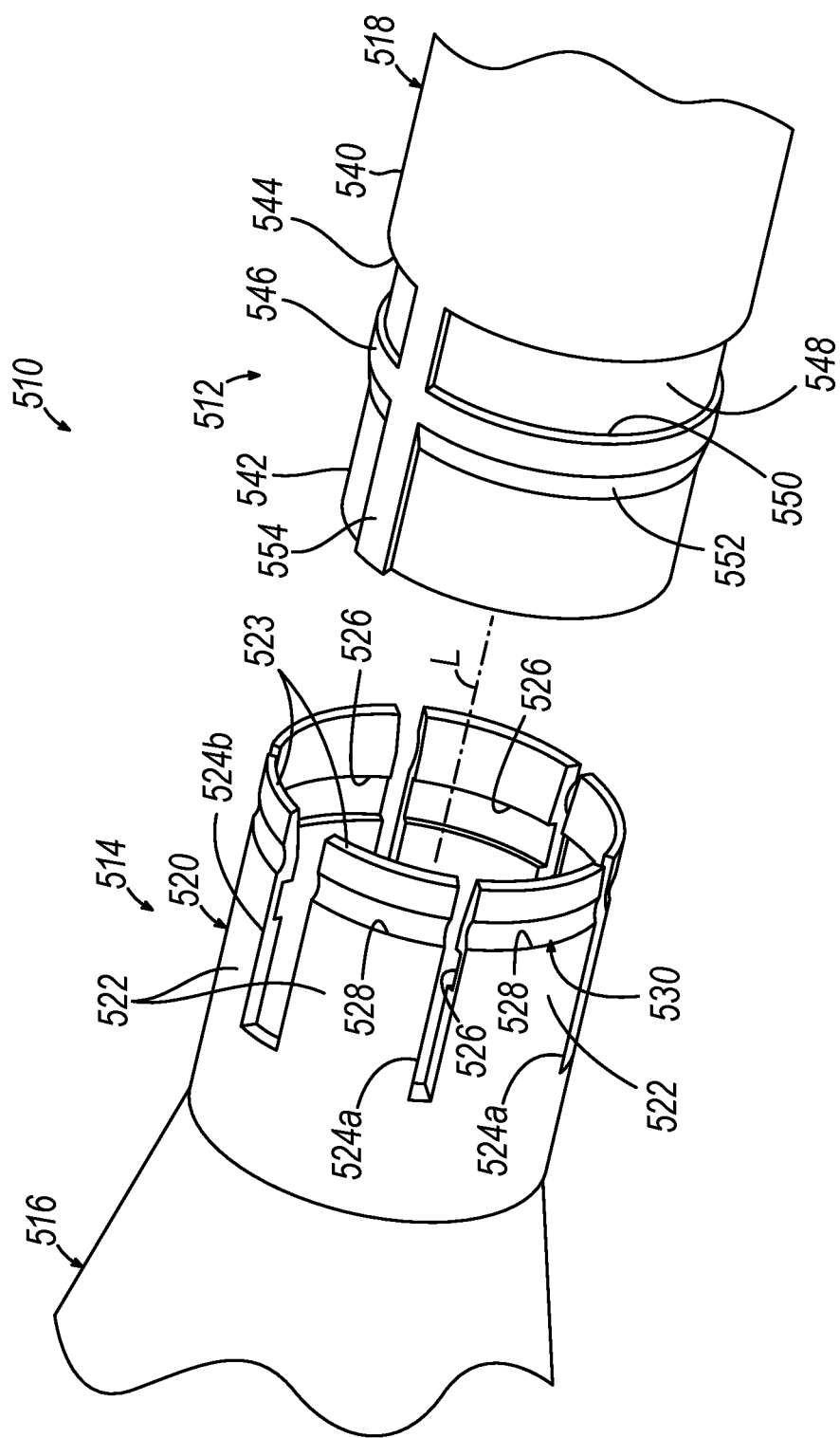
FIG. 8 depicts a partial perspective view of another exemplary circular surgical stapler that includes a shaft assembly and a stapling head assembly, with the shaft assembly and the stapling head assembly shown separated from each other.

A. Exemplary Stapling Head Assembly with Integral Flexible Tabs and Exemplary Shaft Assembly with Corresponding Annular Ridge FIGS. 8-9C show a portion of an exemplary circular surgical stapling instrument (510) that may be used to form anastomosis (70), and including a handle assembly (not shown), such as handle assembly (100), a shaft assembly (512) extending distally from the handle assembly, a stapling head assembly (514) at a distal end of shaft assembly (512), and an anvil (not shown), such as anvil (400), configured to releasably couple and cooperate with stapling head assembly (514) to clamp, staple, and cut tissue. Shaft assembly (512) and stapling head assembly (514) are similar to shaft assembly (200) and stapling head assembly (300) described above, respectively, except as otherwise described below. In this regard, stapling head assembly (514) of this example is coupled to a distal end of shaft assembly (512) and includes a tubular body member (516) and a staple driver member (not shown), such as staple driver member (350), slidably housed therein, and shaft assembly (512) of this example includes an outer sheath (518) that extends between the handle assembly and body member (516) along a longitudinal axis (L).

In the example shown, body member (516) of stapling head assembly (514) includes a proximal expandable collar (520) defined by a plurality of circumferentially-arranged flexible tabs (522) having respective proximal free ends (523). As shown, flexible tabs (522) are spaced apart from each other by respective longitudinal slots (524a, 524b). Slots (524a, 524b) of the present version include a plurality of first slots (524a) having a uniform first width, and a single second slot (524b) having a second width greater than the first width, for reasons described below. In any event, each flexible tab (522) may be integrally formed with a distal remainder of body member (516) and cantilevered relative thereto, such that each flexible tab (522) is configured to flex radially outwardly from an unflexed state (FIGS. 8, 9A, 9C) to a flexed state (FIG. 9B), and is resiliently biased radially inwardly toward the unflexed state. In some versions, body member (516) and, more particularly, collar (520), may be constructed of a plastic material. It will be appreciated that a radially unexpanded state of collar (520) may be defined by each flexible tab (522) being in the respective unflexed state, and that a radially expanded state of collar (520) may be defined by each flexible tab (522) being in the respective flexed state. The integrally formed, cantilevered configurations of flexible tabs (522) relative to the distal remainder of body member (516) may assist in maintaining flexible tabs (522) in their unflexed states in the absence of external forces acting upon flexible tabs (522).

Collar (520) of the present version also includes a plurality of latching features in the form of an annular array of internal arcuate grooves (526) extending radially outwardly from radially inner surfaces of respective flexible tabs (522). Internal arcuate grooves (526) are aligned with each other in the circumferential direction to collectively define a generally annular internal recessed area. Collar (520) further includes a plurality of retention features in the form of an annular array of external arcuate grooves (528) extending radially inwardly from radially outer surfaces of respective flexible tabs (522). External arcuate grooves (528) are aligned with each other in the circumferential direction to collectively define a generally annular external recessed area. As shown, external arcuate grooves (528) are positioned on a proximal collar portion (530) that is disposed proximally relative to internal arcuate grooves (526). It will be appreciated that collar (520) and flexible tabs (522) may be configured and/or arranged in any other suitable manner (s), such as any of those describe below.

In the example shown, outer sheath (518) of shaft assembly (512) includes a relatively wide proximal sheath portion (540) and a relatively narrow distal sheath portion (542) such that an annular shoulder (544) is defined therebetween. In this regard, proximal sheath portion (540) may have a first external diameter substantially greater than an internal diameter of collar (520) to inhibit proximal sheath portion (540) from being received within collar (520), while distal sheath portion (542) may have a second external diameter substantially equal to or slightly less than the internal diameter of collar (520) to permit distal sheath portion (542) to be slidably received within collar (520). In the example shown, annular shoulder (544) is oriented substantially orthogonally relative to longitudinal axis (L).

Outer sheath (518) also includes a protrusion in the form of an annular ridge (546) extending radially outwardly from a radially outer surface of distal sheath portion (542) and spaced apart from shoulder (544) by an external annular channel (548). Annular ridge (546) extends circumferentially about distal sheath portion (542) and has a diameter greater than the internal diameter of collar (520) for urging flexible tabs (522) radially outwardly toward the respective flexed states. For example, the diameter of annular ridge (546) may be substantially equal to or slightly less than that of the generally annular internal recessed area defined by internal arcuate grooves (526) of collar (520) to permit annular ridge (546) to be received within internal arcuate grooves (526) with a snap-fit engagement. In the example shown, external annular channel (548) is also sized to receive proximal collar portion (530) with a snap-fit engagement. Annular ridge (546) of the present version includes a proximal abutment surface (550) oriented substantially orthogonally relative to longitudinal axis (L) and a distal cam surface (552) tapered radially outwardly in the proximal direction.

As shown, outer sheath (518) further includes a longitudinal key (554) extending radially outwardly from the radially outer surface of distal sheath portion (542) and intersecting annular ridge (546). Key (554) may have a width substantially equal to or slightly less than the second width of second slot (524b) and greater than the first width of first slots (524a), such that key (554) is configured to be slidably received within second slot (524b) but is not configured to be slidably received within first slots (524a). In this manner, second slot (524b) may define a keyway for receiving key (554) when shaft assembly (512) and stapling head assembly (514) are angularly oriented relative to each other about longitudinal axis (L) in a predetermined manner. Second slot (524b) and key (554) may thereby cooperate with each other to promote proper angular alignment between shaft assembly (512) and stapling head assembly (514) during coupling of stapling head assembly (514) to shaft assembly (512) and/or to assist in maintaining such proper angular alignment after stapling head assembly (514) has been coupled to shaft assembly (512).

Figure 9A:
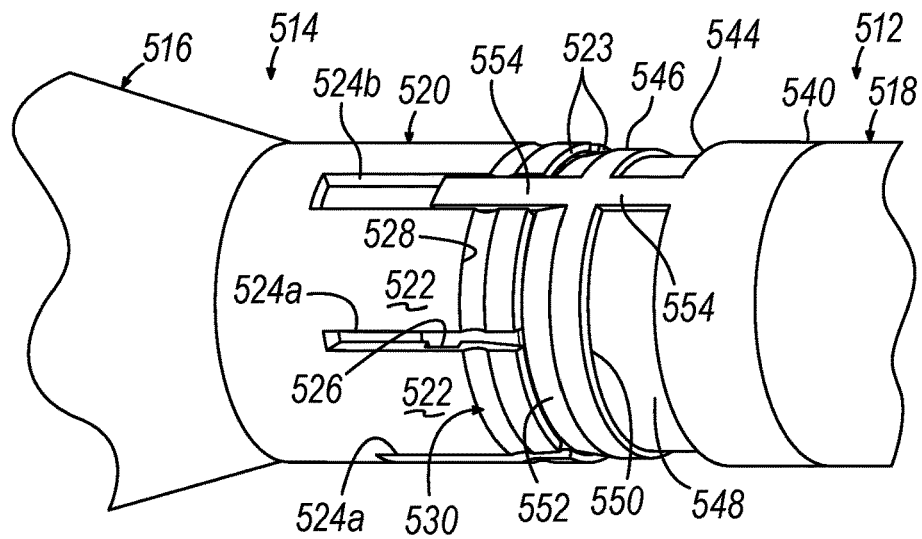
FIG. 9A depicts a partial perspective view of the circular surgical stapler of FIG. 8, showing initial proximal advancement of the stapling head assembly over the shaft assembly with an expandable collar of the stapling head assembly in a radially unexpanded state.
Figure 9B:
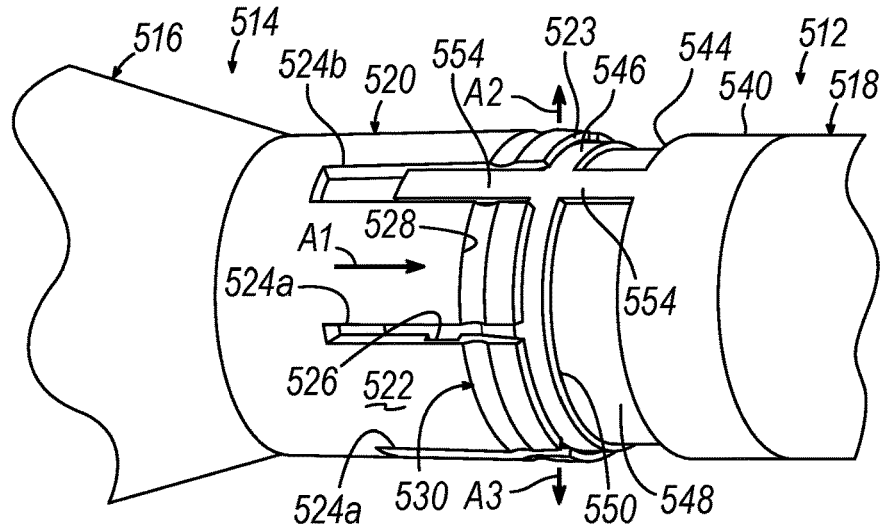
FIG. 9B depicts a partial perspective view of the circular surgical stapler of FIG. 8, showing further proximal advancement of the stapling head assembly over the shaft assembly with the expandable collar urged toward a radially expanded state by an annular ridge of the shaft assembly.
Figure 9C:
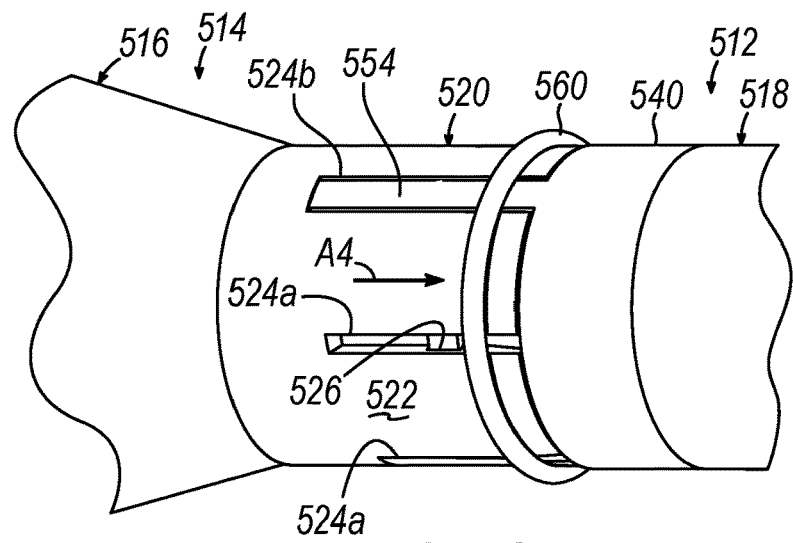
FIG. 9C depicts a partial perspective view of the circular surgical stapler of FIG. 8, showing further proximal advancement of the stapling head assembly over the shaft assembly with the expandable collar returned to the radially unexpanded state to provide a snap-fit engagement between the stapling head assembly and the shaft assembly, with a crimp ring positioned over the expandable collar to secure the expandable collar in the radially unexpanded state.

Referring now to FIGS. 9A-9C, stapling head assembly (514) may be coupled to a distal end of shaft assembly (512) by angularly aligning stapling head assembly (514) with shaft assembly (512) and initially advancing collar (520) proximally over distal sheath portion (542) such that distal sheath portion (542) is slidably received within collar (520) with key (554) slidably received within second slot (524b), as shown in FIG. 9A. During such initial proximal advancement of collar (520), proximal free ends (523) of flexible tabs (522) may be distal of annular ridge (546) thereby permitting flexible tabs (522) to each remain in the respective unflexed state such that collar (520) may be in the radially unexpanded state.

Collar (520) may then continue to be advanced proximally over distal sheath portion (542), as indicated by arrow (A1) in FIG. 9B, to engage distal cam surface (552) of annular ridge (546) with proximal free ends (523) of flexible tabs (522). More particularly, distal cam surface (552) of annular ridge (546) may urge flexible tabs (522) radially outwardly toward the respective flexed states such that collar (520) may be transitioned toward the radially expanded state to permit proximal advancement of collar (520) over annular ridge (546), as indicated by arrows (A2, A3) in FIG. 9B.

As proximal advancement of collar (520) continues, as indicated by arrow (A4) in FIG. 9C, proximal free ends (523) of flexible tabs (522) may be disengaged from distal cam surface (552) of annular ridge (546), and internal arcuate grooves (526) and proximal collar portion (530) may become radially aligned with annular ridge (546) and external annular channel (548), respectively, thereby permitting flexible tabs (522) to resiliently return to their respective unflexed states such that collar (520) may return to the radially unexpanded state. In this regard, annular ridge (546) may be securely received within internal arcuate grooves (526) to provide a snap-fit engagement therebetween, and proximal collar portion (530) may be securely received within external annular channel (548) to provide a snap-fit engagement therebetween. For example, proximal collar portion (530) may be captured between shoulder (544) and abutment surface (550) with internal arcuate grooves (526) latched against abutment surface (550) to inhibit further relative movement between stapling head assembly (514) and shaft assembly (512) along longitudinal axis (L). In some versions, the radial alignment of proximal collar portion (530) with external annular channel (548) may coincide with a hard stop between proximal free ends (523) of flexible tabs (522) and shoulder (544). In any event, second slot (524b) and key (554) may cooperate with each other to inhibit relative rotation between stapling head assembly (514) and shaft assembly (512) about longitudinal axis (L).

In the example shown, a crimp ring (560) is positioned within external arcuate grooves (528) after annular ridge (546) and proximal collar portion (530) have been securely received within internal arcuate grooves (526) and external annular channel (548), respectively, in order to lock flexible tabs (522) in their respective unflexed states such that collar (520) may be securely maintained in the radially unexpanded state. In this manner, crimp ring (560) may assist with inhibiting further relative movement between stapling head assembly (514) and shaft assembly (512) along longitudinal axis (L) by preventing flexible tabs (522) from being urged radially outwardly, thereby preventing collar (520) from being distally retracted over annular ridge (546) or proximally advanced over shoulder (544). Crimp ring (560) of the present version is radially aligned with external annular channel (548) to clamp proximal free ends (523) of flexible tabs (522) within external annular channel (548). Crimp ring (560) may be tightly secured within external arcuate grooves (528) via crimping or any other suitable technique. In this regard, crimp ring (560) may be constructed of a ductile material, such as a metallic material.

Thus, stapling head assembly (514) and shaft assembly (512) may be securely and reliably coupled to each other in the manner set forth above, and may subsequently be used to perform an anastomosis procedure.

Figure 10A:
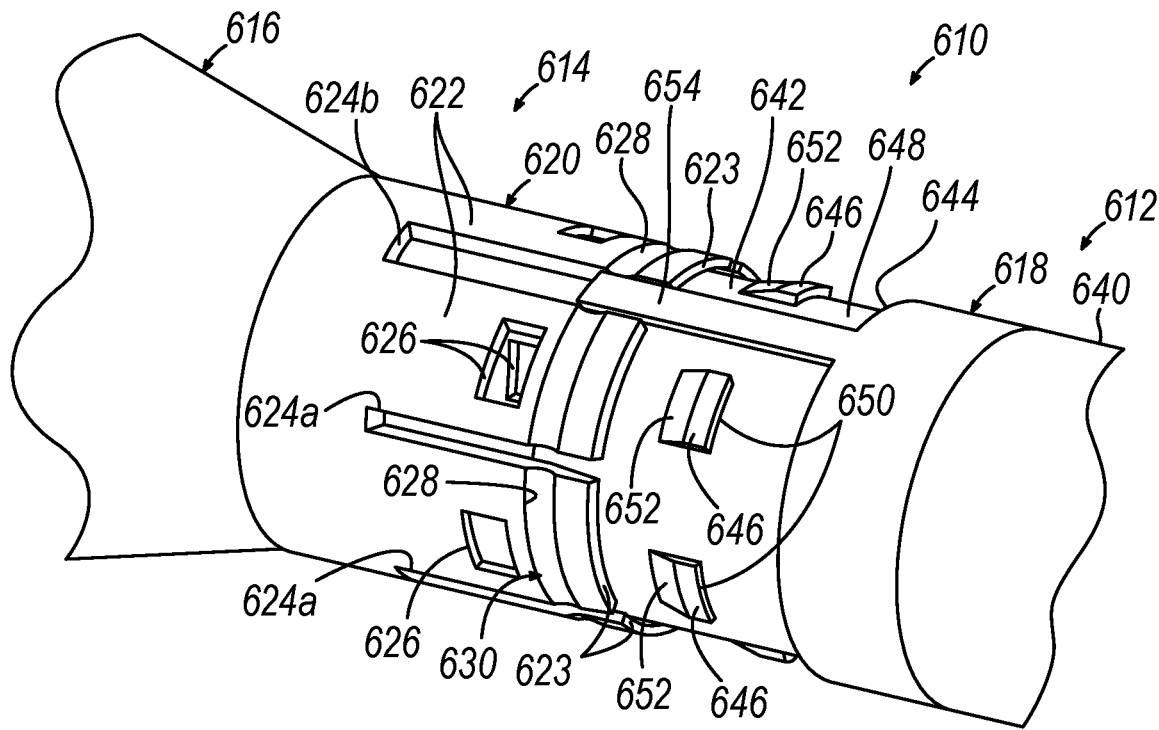
FIG. 10A depicts a partial perspective view of another exemplary circular surgical stapler that includes a shaft assembly and a stapling head assembly, showing initial proximal advancement of the stapling head assembly over the shaft assembly with an expandable collar of the stapling head assembly in a radially unexpanded state.
Figure 10B:
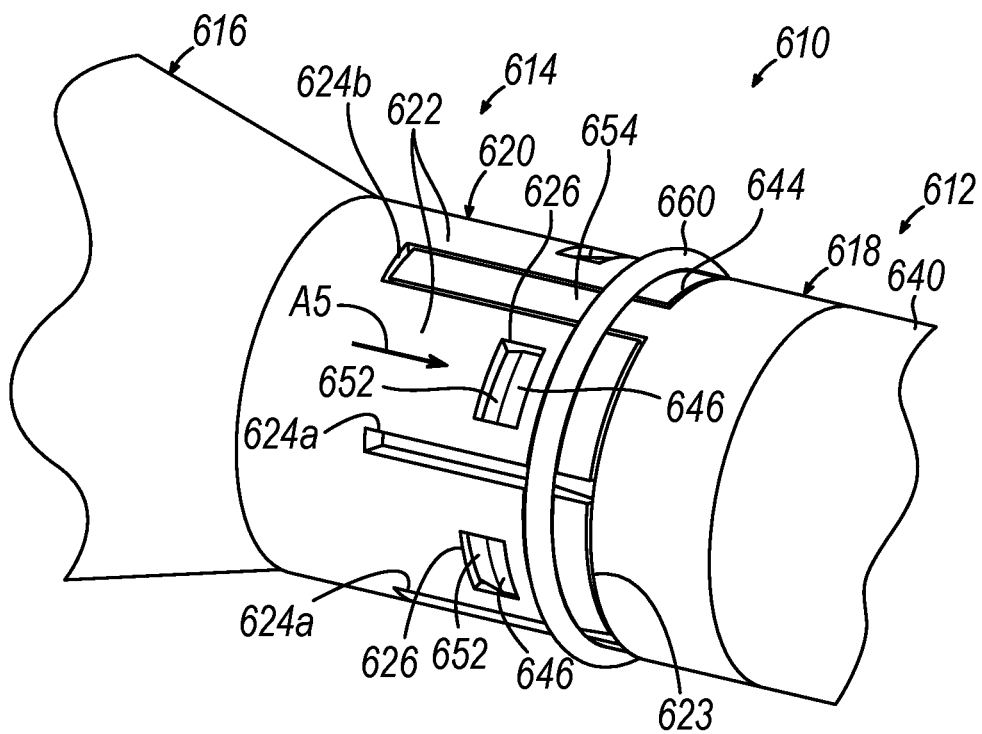
FIG. 10B depicts a partial perspective view of the circular surgical stapler of FIG. 10A, showing further proximal advancement of the stapling head assembly over the shaft assembly with the expandable collar returned to the radially unexpanded state after being urged toward a radially expanded state by an annular array of detents of the shaft assembly to provide a snap-fit engagement between the stapling head assembly and the shaft assembly, with a crimp ring positioned over the expandable collar to secure the expandable collar in the radially unexpanded state.

B. Exemplary Stapling Head Assembly with Integral Flexible Tabs and Exemplary Shaft Assembly with Corresponding Detents FIGS. 10A-10B show a portion of another exemplary circular surgical stapling instrument (610) that may be used to form anastomosis (70), and including a handle assembly (not shown), such as handle assembly (100), a shaft assembly (612) extending distally from the handle assembly, a stapling head assembly (614) at a distal end of shaft assembly (612), and an anvil (not shown), such as anvil (400), configured to releasably couple and cooperate with stapling head assembly (614) to clamp, staple, and cut tissue. Shaft assembly (612) and stapling head assembly (614) are similar to shaft assembly (512) and stapling head assembly (514) described above, respectively, except as otherwise described below. In this regard, stapling head assembly (614) of this example is coupled to a distal end of shaft assembly (612) and includes a tubular body member (616) and a staple driver member (not shown), such as staple driver member (350), slidably housed therein, and shaft assembly (612) of this example includes an outer sheath (618) that extends between the handle assembly and body member (616) along a longitudinal axis (not shown).

In the example shown, body member (616) of stapling head assembly (614) includes a proximal expandable collar (620) defined by a plurality of circumferentially-arranged flexible tabs (622) having respective proximal free ends (623). As shown, flexible tabs (622) are spaced apart from each other by respective longitudinal slots (624a, 624b). Slots (624a, 624b) of the present version include a plurality of first slots (624a) having a uniform first width, and a single second slot (624b) having a second width greater than the first width, for reasons described below. In any event, each flexible tab (622) may be integrally formed with a distal remainder of body member (616) and cantilevered relative thereto, such that each flexible tab (622) is configured to flex radially outwardly from the illustrated unflexed state to a flexed state (not shown), and is resiliently biased radially inwardly toward the unflexed state. In some versions, body member (616) and, more particularly, collar (620), may be constructed of a plastic material. It will be appreciated that a radially unexpanded state of collar (620) may be defined by each flexible tab (622) being in the respective unflexed state, and that a radially expanded state of collar (620) may be defined by each flexible tab (622) being in the respective flexed state. The integrally formed, cantilevered configurations of flexible tabs (622) relative to the distal remainder of body member (616) may assist in maintaining flexible tabs (622) in their unflexed states in the absence of external forces acting upon flexible tabs (622).

Collar (620) of the present version also includes a plurality of latching features in the form of an annular array of apertures (626) extending radially through respective flexible tabs (622). Collar (620) further includes a plurality of retention features in the form of an annular array of external arcuate grooves (628) extending radially inwardly from radially outer surfaces of respective flexible tabs (622). External arcuate grooves (628) are aligned with each other in the circumferential direction to collectively define a generally annular external recessed area. As shown, external arcuate grooves (628) are positioned on a proximal collar portion (630) that is disposed proximally relative to apertures (626). It will be appreciated that collar (620) and flexible tabs (622) may be configured and/or arranged in any other suitable manner(s), such as any of those describe below.

In the example shown, outer sheath (618) of shaft assembly (612) includes a relatively wide proximal sheath portion (640) and a relatively narrow distal sheath portion (642) such that an annular shoulder (644) is defined therebetween. In this regard, proximal sheath portion (640) may have a first external diameter substantially greater than an internal diameter of collar (620) to inhibit proximal sheath portion (640) from being received within collar (620), while distal sheath portion (642) may have a second external diameter substantially equal to or slightly less than the internal diameter of collar (620) to permit distal sheath portion (642) to be slidably received within collar (620). In the example shown, annular shoulder (644) is oriented substantially orthogonally relative to the longitudinal axis.

Outer sheath (618) also includes a plurality of protrusions in the form of an annular array of detents (646) extending radially outwardly from a radially outer surface of distal sheath portion (642) for radial alignment with corresponding apertures (626) of collar (620), and spaced apart from shoulder (644) by an external, generally annular channel (648). Annular detents (646) are arranged circumferentially about distal sheath portion (642) and collectively have a diameter greater than the internal diameter of collar (620) for urging corresponding flexible tabs (622) radially outwardly toward the respective flexed states. Moreover, each detent (646) may have length and width dimensions substantially equal to or slightly less than those of apertures (626) of collar (620) to permit detents (646) to be received within corresponding apertures (626) with a snap-fit engagement. In the example shown, external annular channel (648) is also sized to receive proximal collar portion (630) with a snap-fit engagement. Each detent (646) of the present version includes a proximal abutment surface (650) oriented substantially orthogonally relative to the longitudinal axis and a distal cam surface (652) tapered radially outwardly in the proximal direction.

As shown, outer sheath (618) further includes a longitudinal key (654) extending radially outwardly from the radially outer surface of distal sheath portion (642). Key (654) may have a width substantially equal to or slightly less than the second width of second slot (624b) and greater than the first width of first slots (624a), such that key (654) is configured to be slidably received within second slot (624b) but is not configured to be slidably received within first slots (624a). In this manner, second slot (624b) may define a keyway for receiving key (654) when shaft assembly (612) and stapling head assembly (614) are angularly oriented relative to each other about the longitudinal axis in a predetermined manner. Second slot (624b) and key (654) may thereby cooperate with each other to promote proper angular alignment between shaft assembly (612) and stapling head assembly (614) during coupling of stapling head assembly (614) to shaft assembly (612) and/or to assist in maintaining such proper angular alignment after stapling head assembly (614) has been coupled to shaft assembly (612).

With continuing reference to FIGS. 10A-10B, stapling head assembly (614) may be coupled to a distal end of shaft assembly (612) by angularly aligning stapling head assembly (614) with shaft assembly (612) and initially advancing collar (620) proximally over distal sheath portion (642) such that distal sheath portion (642) is slidably received within collar (620) with key (654) slidably received within second slot (624b), as shown in FIG. 10A. During such initial proximal advancement of collar (620), proximal free ends (623) of flexible tabs (622) may be distal of detents (646) thereby permitting flexible tabs (622) to each remain in the respective unflexed state such that collar (620) may be in the radially unexpanded state.

Collar (620) may then continue to be advanced proximally over distal sheath portion (642) to engage distal cam surfaces (652) of detents (646) with proximal free ends (623) of corresponding flexible tabs (622), in a manner similar to that described above in connection with FIGS. 9A-9C. More particularly, distal cam surfaces (652) of detents (646) may urge the corresponding flexible tabs (622) radially outwardly toward the respective flexed states such that collar (620) may be transitioned toward the radially expanded state to permit proximal advancement of collar (620) over detents (646).

As proximal advancement of collar (620) continues, as indicated by arrow (A5) in FIG. 10B, proximal free ends (623) of flexible tabs (622) may be disengaged from distal cam surfaces (652) of detents (646), and apertures (626) and proximal collar portion (630) may become radially aligned with detents (646) and external annular channel (648), respectively, thereby permitting flexible tabs (622) to resiliently return to their respective unflexed states such that collar (620) may return to the radially unexpanded state, as shown in FIG. 9B. In this regard, detents (646) may be securely received within corresponding apertures (626) to provide a snap-fit engagement therebetween, and proximal collar portion (630) may be securely received within external annular channel (648) to provide a snap-fit engagement therebetween. For example, proximal collar portion (630) may be captured between shoulder (644) and abutment surfaces (650) with apertures (626) latched against abutment surfaces (650) to inhibit further relative movement between stapling head assembly (614) and shaft assembly (612) along the longitudinal axis. In some versions, the radial alignment of proximal collar portion (630) with external annular channel (648) may coincide with a hard stop between proximal free ends (623) of flexible tabs (622) and shoulder (644). In any event, second slot (624b) and key (654) may cooperate with each other to inhibit relative rotation between stapling head assembly (614) and shaft assembly (612) about the longitudinal axis.

In the example shown, a crimp ring (660) is positioned within external arcuate grooves (628) after detents (646) and proximal collar portion (630) have been securely received within apertures (626) and external annular channel (648), respectively, in order to lock flexible tabs (622) in their respective unflexed states such that collar (620) may be securely maintained in the radially unexpanded state. In this manner, crimp ring (660) may assist with inhibiting further relative movement between stapling head assembly (614) and shaft assembly (612) along the longitudinal axis by preventing flexible tabs (622) from being urged radially outwardly, thereby preventing collar (620) from being distally retracted over detents (646) or proximally advanced over shoulder (644). Crimp ring (660) of the present version is radially aligned with external annular channel (648) to clamp proximal free ends (623) of flexible tabs (622) within external annular channel (648). Crimp ring (660) may be tightly secured within external arcuate grooves (628) via crimping or any other suitable technique. In this regard, crimp ring (660) may be constructed of a ductile material, such as a metallic material.

Thus, stapling head assembly (614) and shaft assembly (612) may be securely and reliably coupled to each other in the manner set forth above, and may subsequently be used to perform an anastomosis procedure.

Figure 11:
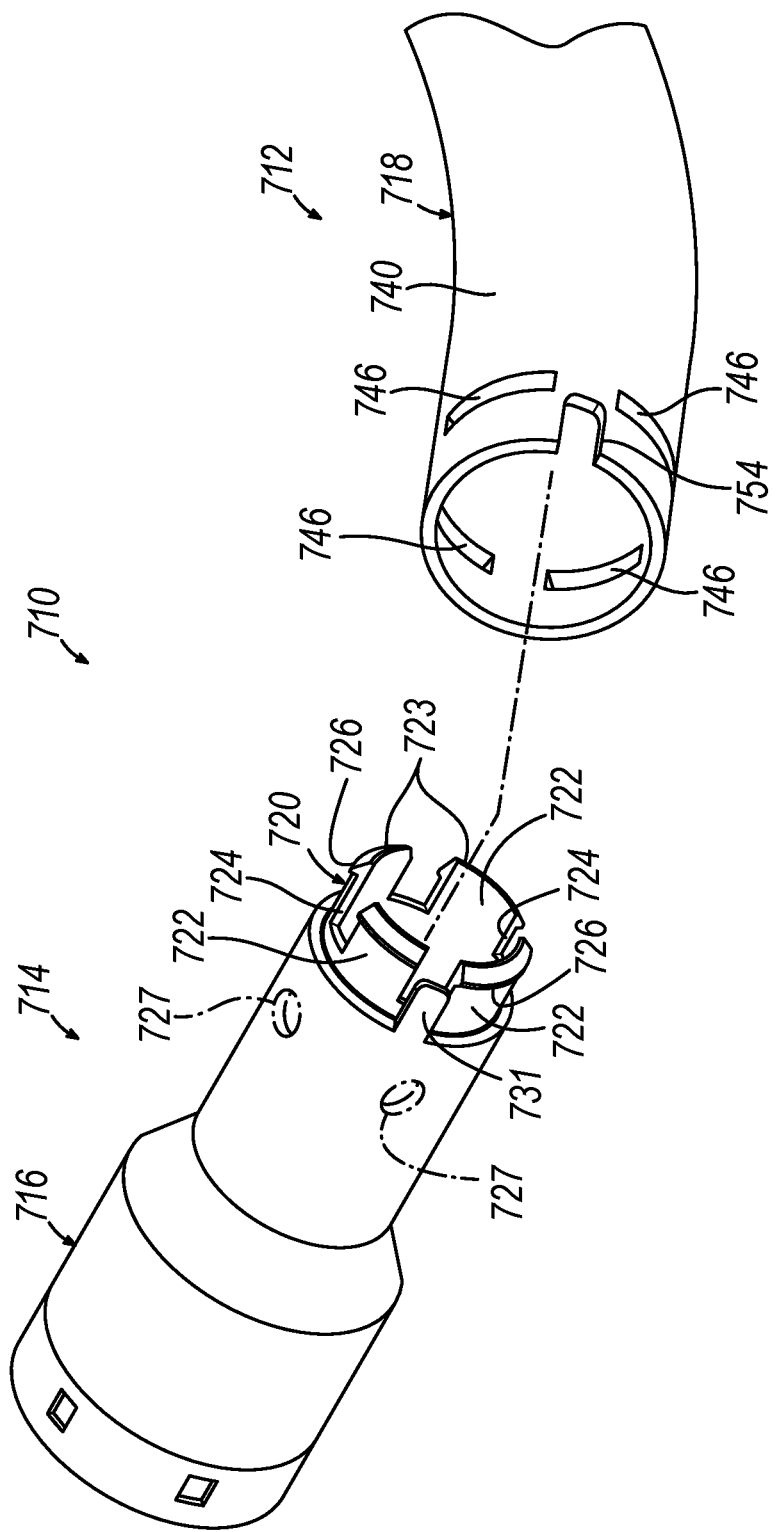
FIG. 11 depicts a partial perspective view of another exemplary circular surgical stapler that includes a shaft assembly and a stapling head assembly, with the shaft assembly and the stapling head assembly shown separated from each other, showing a contractable collar of the stapling head assembly and an annular array of apertures of the shaft assembly configured to cooperate with each other to provide a snap-fit engagement between the stapling head assembly and the shaft assembly.

C. Exemplary Stapling Head Assembly Overmolded onto Collar with Flexible Tabs and Exemplary Shaft Assembly with Corresponding Apertures FIG. 11 shows a portion of another exemplary circular surgical stapling instrument (710) that may be used to form anastomosis (70), and including a handle assembly (not shown), such as handle assembly (100), a shaft assembly (712) extending distally from the handle assembly, a stapling head assembly (714) at a distal end of shaft assembly (712), and an anvil (not shown), such as anvil (400), configured to releasably couple and cooperate with stapling head assembly (714) to clamp, staple, and cut tissue. Shaft assembly (712) and stapling head assembly (714) are similar to shaft assembly (512) and stapling head assembly (514) described above, respectively, except as otherwise described below. In this regard, stapling head assembly (714) of this example is coupled to a distal end of shaft assembly (712) and includes a tubular body member (716) and a staple driver member (not shown), such as staple driver member (350), slidably housed therein, and shaft assembly (712) of this example includes an outer sheath (718) that extends between the handle assembly and body member (716).

In the example shown, stapling head assembly (714) includes a proximal contractable collar (720) separately formed from and fixedly secured to body member (716) and including a plurality of circumferentially-arranged flexible tabs (722) having respective proximal free ends (723). As shown, flexible tabs (722) are spaced apart from each other by respective longitudinal slots (724). Each flexible tab (722) may be integrally formed with a distal remainder of collar (720) and cantilevered relative thereto, such that each flexible tab (722) is configured to flex radially inwardly from the illustrated unflexed state to a flexed state (not shown), and is resiliently biased radially outwardly toward the unflexed state. Collar (720) of the present version also includes a plurality of latching features in the form of an annular array of detents (726) extending radially outwardly from respective flexible tabs (722) at or near the respective free ends (723) thereof, as well as an annular array of overmolding features in the form of apertures (727) for receiving flowable material of body member (716) during overmolding of body member (716) onto collar (720). In this regard, collar (720) may be constructed of a metallic material, for example. While body member (716) of the present example is overmolded onto collar (720), it will be appreciated that body member (716) may be fixedly secured to collar (720) in any other suitable manner. In any event, body member (716) includes a proximally-extending key (731) disposed radially outwardly of collar (720).

In the example shown, outer sheath (718) of shaft assembly (712) includes a sheath portion (740) having an internal diameter less than an external diameter collectively defined by detents (726) for urging flexible tabs (722) radially inwardly toward the respective flexed states. Outer sheath (718) also includes an annular array of apertures (746) extending radially through a distal portion of outer sheath (718) for radial alignment with corresponding detents (726) of collar (720). Each aperture (746) may have length and width dimensions substantially equal to or slightly greater than those of detents (726) of collar (720) to permit detents (726) to be received within corresponding apertures (746) with a snap-fit engagement. As shown, outer sheath (718) further includes a longitudinal keyway (754) extending proximally from a distal end of outer sheath (718) and configured to cooperate with key (731) to promote proper angular alignment between shaft assembly (712) and stapling head assembly (714).

Figure 12:
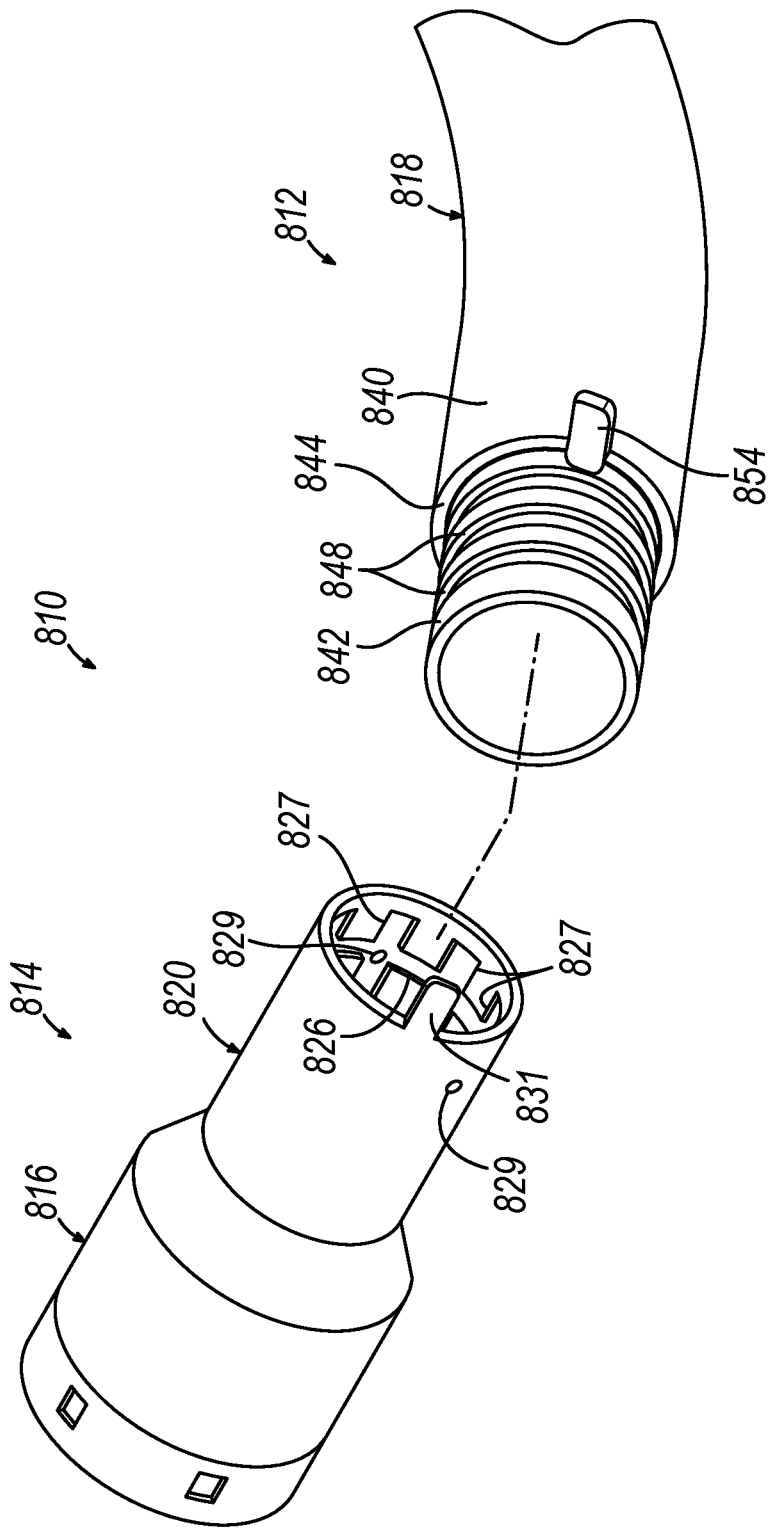
FIG. 12 depicts a partial perspective view of another exemplary circular surgical stapler that includes a shaft assembly and a stapling head assembly, with the shaft assembly and the stapling head assembly shown separated from each other, showing various adhesive-directing grooves of the stapling head assembly and the shaft assembly configured to cooperate with each other to provide improved adhesion between the stapling head assembly and the shaft assembly.

D. Exemplary Stapling Head Assembly and Shaft Assembly with Adhesive Distribution Grooves FIG. 12 shows a portion of another exemplary circular surgical stapling instrument (810) that may be used to form anastomosis (70), and including a handle assembly (not shown), such as handle assembly (100), a shaft assembly (812) extending distally from the handle assembly, a stapling head assembly (814) at a distal end of shaft assembly (812), and an anvil (not shown), such as anvil (400), configured to releasably couple and cooperate with stapling head assembly (814) to clamp, staple, and cut tissue. Shaft assembly (812) and stapling head assembly (814) are similar to shaft assembly (512) and stapling head assembly (514) described above, respectively, except as otherwise described below. In this regard, stapling head assembly (814) of this example is coupled to a distal end of shaft assembly (812) and includes a tubular body member (816) and a staple driver member (not shown), such as staple driver member (350), slidably housed therein, and shaft assembly (812) of this example includes an outer sheath (818) that extends between the handle assembly and body member (816).

In the example shown, body member (816) of stapling head assembly (814) includes a proximal collar (820) including an internal annular groove (826) extending radially outwardly from a radially inner surface of collar (820). Collar (820) also includes a plurality of circumferentially-arranged internal longitudinal grooves (827) extending radially outwardly from the radially inner surface of collar (820) and intersecting internal annular groove (826) at or near their respective midpoints. In this manner, internal longitudinal grooves (827) may be configured to distribute a flowable adhesive (not shown) both proximally and distally therealong from internal annular groove (826). As shown, collar (820) further includes a plurality of adhesive injection ports (829) extending radially through a proximal portion of collar (820) in fluid communication with internal annular groove (826) to facilitate injection of the flowable adhesive into internal annular groove (826) from an exterior of collar (820) for subsequent distribution by internal longitudinal grooves (827). Collar (820) of the present example also includes a proximally-extending key (831).

In the example shown, outer sheath (818) of shaft assembly (812) includes a relatively wide proximal sheath portion (840) and a relatively narrow distal sheath portion (842) such that an annular shoulder (844) is defined therebetween. In this regard, proximal sheath portion (840) may have a first external diameter substantially greater than an internal diameter of collar (820) to inhibit proximal sheath portion (840) from being received within collar (820), while distal sheath portion (842) may have a second external diameter substantially equal to or slightly less than the internal diameter of collar (820) to permit distal sheath portion (842) to be slidably received within collar (820). Outer sheath (818) also includes a plurality of external annular grooves (848) extending radially inwardly from a radially outer surface of distal sheath portion (842). Each external annular groove (848) is configured to be at least partially radially aligned with internal longitudinal grooves (827) of collar (820) for fluid communication therewith. In this manner, external annular grooves (848) may be configured to distribute the flowable adhesive circumferentially therealong from internal longitudinal grooves (827) (and/or from internal annular groove (826)) to promote even distribution of the flowable adhesive through internal annular groove (826), internal longitudinal grooves (827), and external annular grooves (848) to securely adhere distal sheath portion (842) to collar (820). In some versions, the flowable adhesive may include an ultraviolet-curable (also referred to as "UV-curable") resin. In this regard, body member (816) and, more particularly, collar (820), may be constructed of a transparent and/or translucent material, such as a plastic material (e.g., polyetherimide, polycarbonate, or other suitable plastic material) for permitting the passage of ultraviolet light therethrough and/or for permitting a user to observe the adhesive therethrough. As shown, outer sheath (818) further includes a longitudinal keyway (854) extending proximally from a distal end of proximal sheath portion (840) and configured to cooperate with key (831) to promote proper angular alignment between shaft assembly (812) and stapling head assembly (814).

E. Exemplary Stapling Head Assembly and Shaft Assembly with Welded Collar

Figure 13:
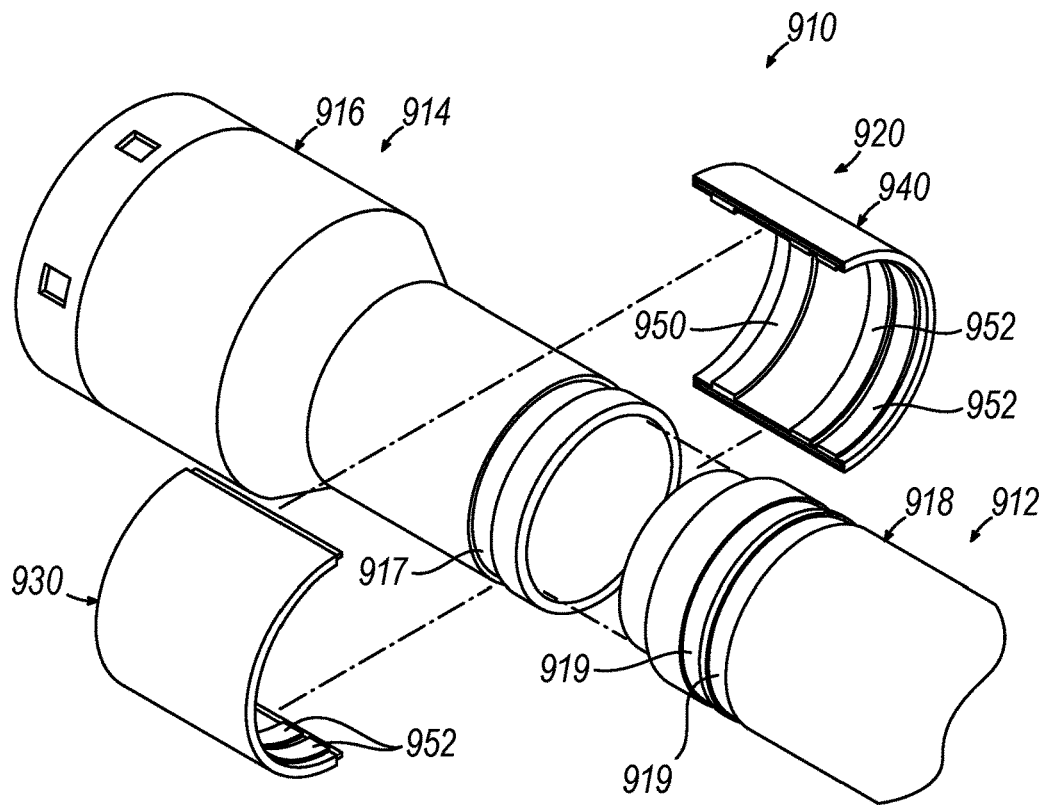
FIG. 13 depicts a partial disassembled perspective view of another exemplary circular surgical stapler that includes a shaft assembly and a stapling head assembly, with the shaft assembly and the stapling head assembly shown separated from each other, showing a welded collar configured to be fixedly secured over a proximal portion of the stapling head assembly and a distal portion of the shaft assembly.
Figure 14:
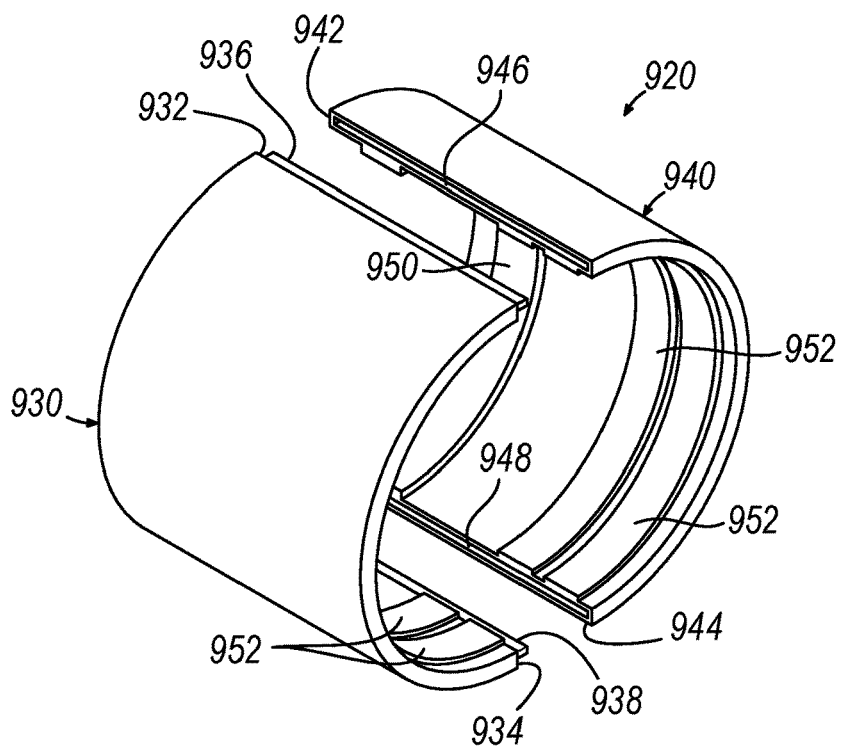
FIG. 14 depicts a perspective view of the welded collar of FIG. 13, with first and second semicylindrical collar portions of the welded collar shown separated from each other.

FIGS. 13-14 show a portion of another exemplary circular surgical stapling instrument (910) that may be used to form anastomosis (70), and including a handle assembly (not shown), such as handle assembly (100), a shaft assembly (912) extending distally from the handle assembly, a stapling head assembly (914) at a distal end of shaft assembly (912), and an anvil (not shown), such as anvil (400), configured to releasably couple and cooperate with stapling head assembly (914) to clamp, staple, and cut tissue. Shaft assembly (912) and stapling head assembly (914) are similar to shaft assembly (512) and stapling head assembly (514) described above, respectively, except as otherwise described below. In this regard, stapling head assembly (914) of this example is coupled to a distal end of shaft assembly (912) and includes a tubular body member (916) and a staple driver member (not shown), such as staple driver member (350), slidably housed therein, and shaft assembly (912) of this example includes an outer sheath (918) that extends between the handle assembly and body member (916). As shown, body member (916) includes an external annular groove (917) extending radially inwardly from a radially outer surface of body member (916), and outer sheath (918) also includes a pair of external annular grooves (919) extending radially inwardly from a radially outer surface of outer sheath (918).

In the example shown, instrument (910) further includes a welded collar (920) fixedly secured over a proximal portion of body member (916) and a distal portion of outer sheath (918). As shown, collar (920) includes a first semicylindrical collar portion (930) extending between first and second longitudinal edges (932, 934), with first and second energy directors (936, 938) extending beyond first and second longitudinal edges (932, 934), respectively. Collar (920) also includes a second semicylindrical collar portion (940) extending between third and fourth longitudinal edges (942, 944), with first and second energy wells (946, 948) recessed relative to third and fourth longitudinal edges (942, 944) for receiving first and second energy directors (936, 938), respectively. In this manner, energy directors (936, 938) may cooperate with the corresponding energy wells (946, 948) to facilitate ultrasonic welding of collar portions (930, 940) to each other along the corresponding longitudinal edges (932, 934, 942, 944). In this regard, collar portions (930, 940) may each be constructed of an ultrasonically weldable material such a polycarbonate, for example. In the example shown, a distal semi-annular ridge (950) and a pair of proximal semi-annular ridges (952) extend radially inwardly from a radially inner surface of each collar portion (930, 940) for receipt within external annular groove (917) of body member (916) and external annular grooves (919) of outer sheath (918), respectively.

While collar portions (930, 940) of the present example are ultrasonically welded to each other, it will be appreciated that collar portions (930, 940) may be fixedly secured to each other in any other suitable manner. In some versions, one of first or second collar portions (930, 940) may be integrally formed together with body member (916) as a unitary piece, and the other of first or second collar portions (930, 940) may be fixedly secured to the one of collar portions (930, 940) with the distal portion of outer sheath (918) captured between collar portions (930, 940).

F. Exemplary Stapling Head Assembly and Shaft Assembly with Hinged Collar

Figure 15:
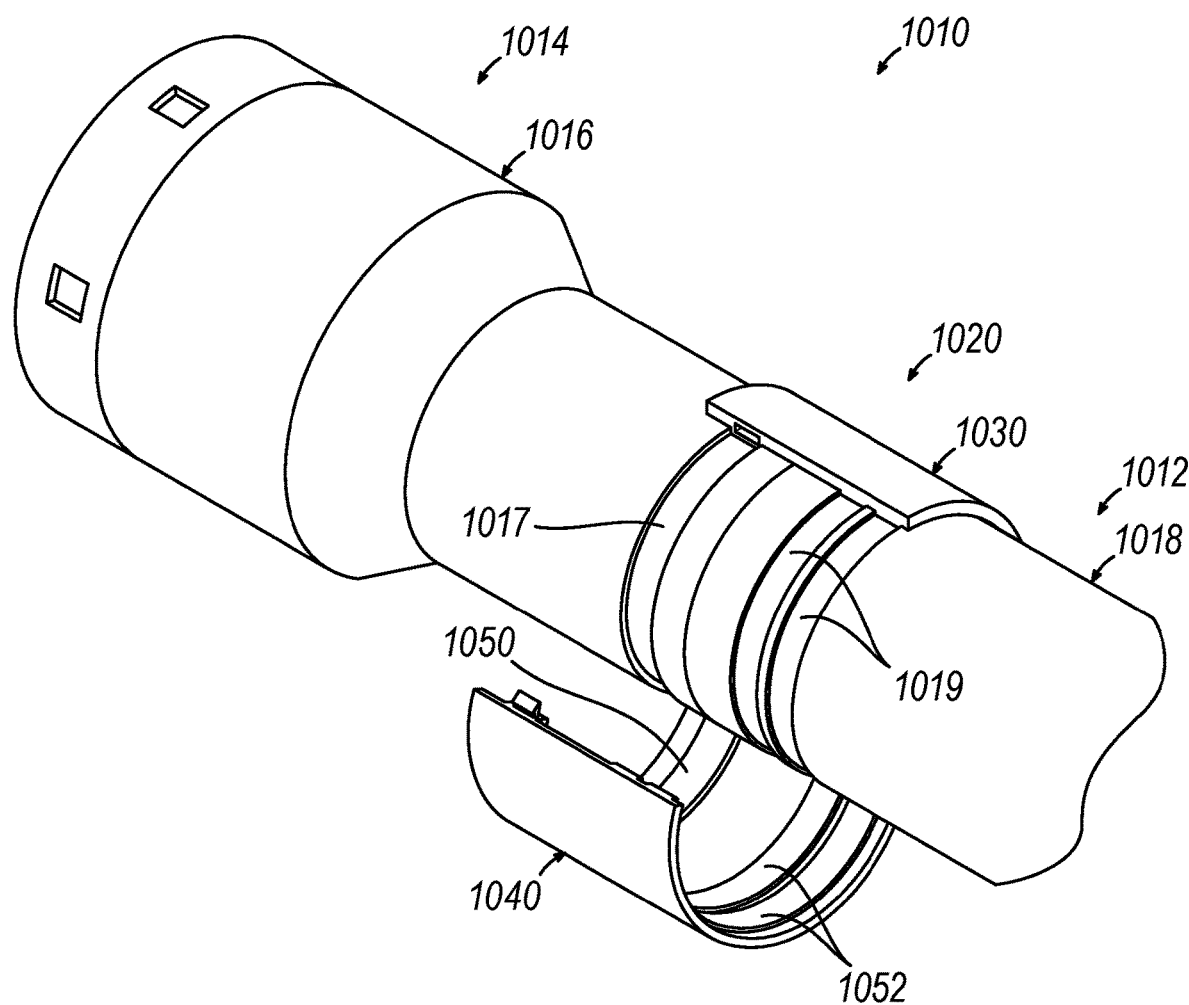
FIG. 15 depicts a partial perspective view of another exemplary circular surgical stapler that includes a shaft assembly and a stapling head assembly, showing a hinged collar configured to be fixedly secured over a proximal portion of the stapling head assembly and a distal portion of the shaft assembly.
Figure 16:
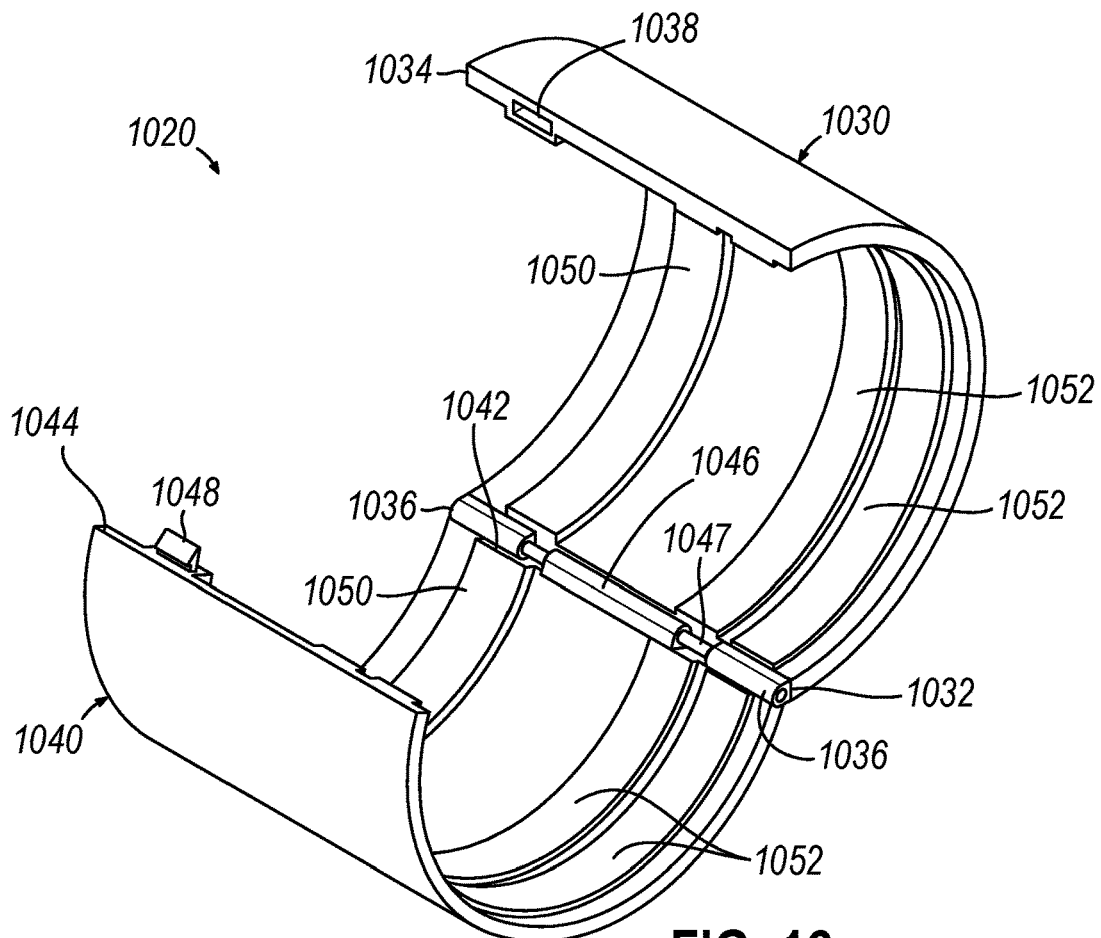
FIG. 16 depicts a perspective view of the hinged collar of FIG. 15, with first and second semicylindrical collar portions of the hinged collar shown pivoted away from each other.

FIGS. 15-17 show a portion of another exemplary circular surgical stapling instrument (1010) that may be used to form anastomosis (70), and including a handle assembly (not shown), such as handle assembly (100), a shaft assembly (1012) extending distally from the handle assembly, a stapling head assembly (1014) at a distal end of shaft assembly (1012), and an anvil (not shown), such as anvil (400), configured to releasably couple and cooperate with stapling head assembly (1014) to clamp, staple, and cut tissue. Shaft assembly (1012) and stapling head assembly (1014) are similar to shaft assembly (512) and stapling head assembly (514) described above, respectively, except as otherwise described below. In this regard, stapling head assembly (1014) of this example is coupled to a distal end of shaft assembly (1012) and includes a tubular body member (1016) and a staple driver member (not shown), such as staple driver member (350), slidably housed therein, and shaft assembly (1012) of this example includes an outer sheath (1018) that extends between the handle assembly and body member (1016). As shown, body member (1016) includes an external annular groove (1017) extending radially inwardly from a radially outer surface of body member (1016), and outer sheath (1018) also includes a pair of external annular grooves (1019) extending radially inwardly from a radially outer surface of outer sheath (1018).

Figure 17A:
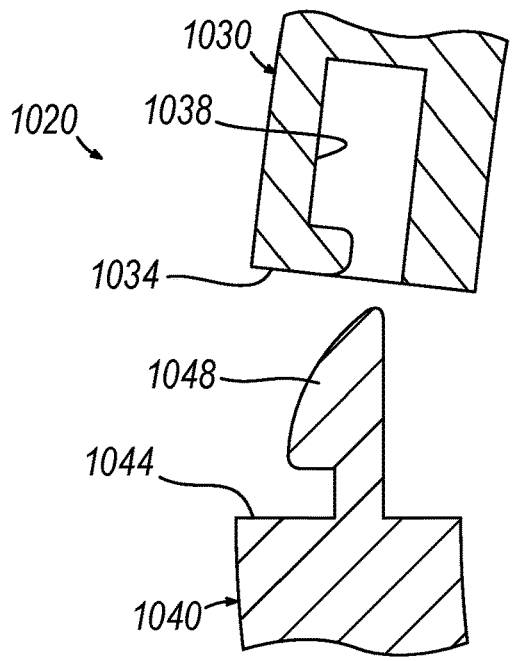
FIG. 17A depicts a partial cross-sectional view of the hinged collar of FIG. 15 with the first and second semicylindrical collar portions of the hinged collar shown pivoted away from each other such that a clip of the second semicylindrical collar portion is disengaged from a corresponding pocket of the first semicylindrical collar portion.
Figure 17B:
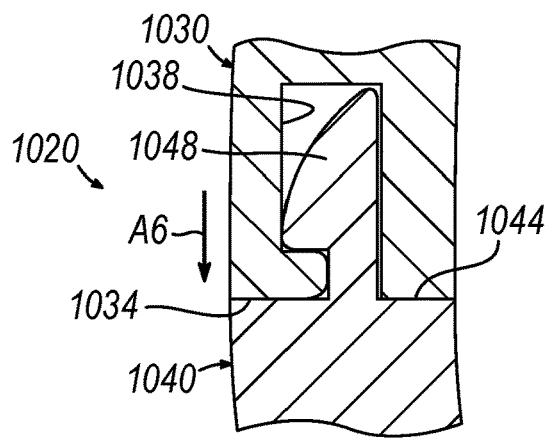
FIG. 17B depicts a partial cross-sectional view of the hinged collar of FIG. 15 with the first and second semicylindrical collar portions of the hinged collar shown pivoted toward each other such that the clip of the second semicylindrical collar portion is engaged with the corresponding pocket of the first semicylindrical collar portion.

In the example shown, instrument (1010) further includes a hinged collar (1020) fixedly secured over a proximal portion of body member (1016) and a distal portion of outer sheath (1018). As shown, collar (1020) includes a first semicylindrical collar portion (1030) extending between first and second longitudinal edges (1032, 1034), with at least one first hinge (1036) positioned at or near first longitudinal edge (1032) and at least one pocket (1038) recessed relative to second longitudinal edge (1034). Collar (1020) also includes a second semicylindrical collar portion (1040) extending between third and fourth longitudinal edges (1042, 1044), with at least one second hinge (1046) positioned at or near third longitudinal edge (1042) for pivotably coupling with first hinge (1036) via a pin (1047), and with at least one flexible clip (1048) extending beyond fourth longitudinal edges (1044) for receipt within pocket (1038). In this manner, pocket (1038) may cooperate with flexible clip (1048) to provide a snap-fit engagement therebetween, as shown in FIGS. 17A-17B (e.g., with relative movement between collar portions (1030, 1040) indicated by arrow (A6) in FIG. 17B). In some versions, collar portions (1030, 1040) may be laser welded to each other along the corresponding longitudinal edges (932, 934, 942, 944). In this regard, collar portions (1030, 1040) may each be constructed of a laser weldable material such as a metallic material, for example. In the example shown, a distal semi-annular ridge (1050) and a pair of proximal semi-annular ridges (1052) extend radially inwardly from a radially inner surface of each collar portion (1030, 1040) for receipt within external annular groove (1017) of body member (1016) and external annular grooves (1019) of outer sheath (1018), respectively.

Figure 18:
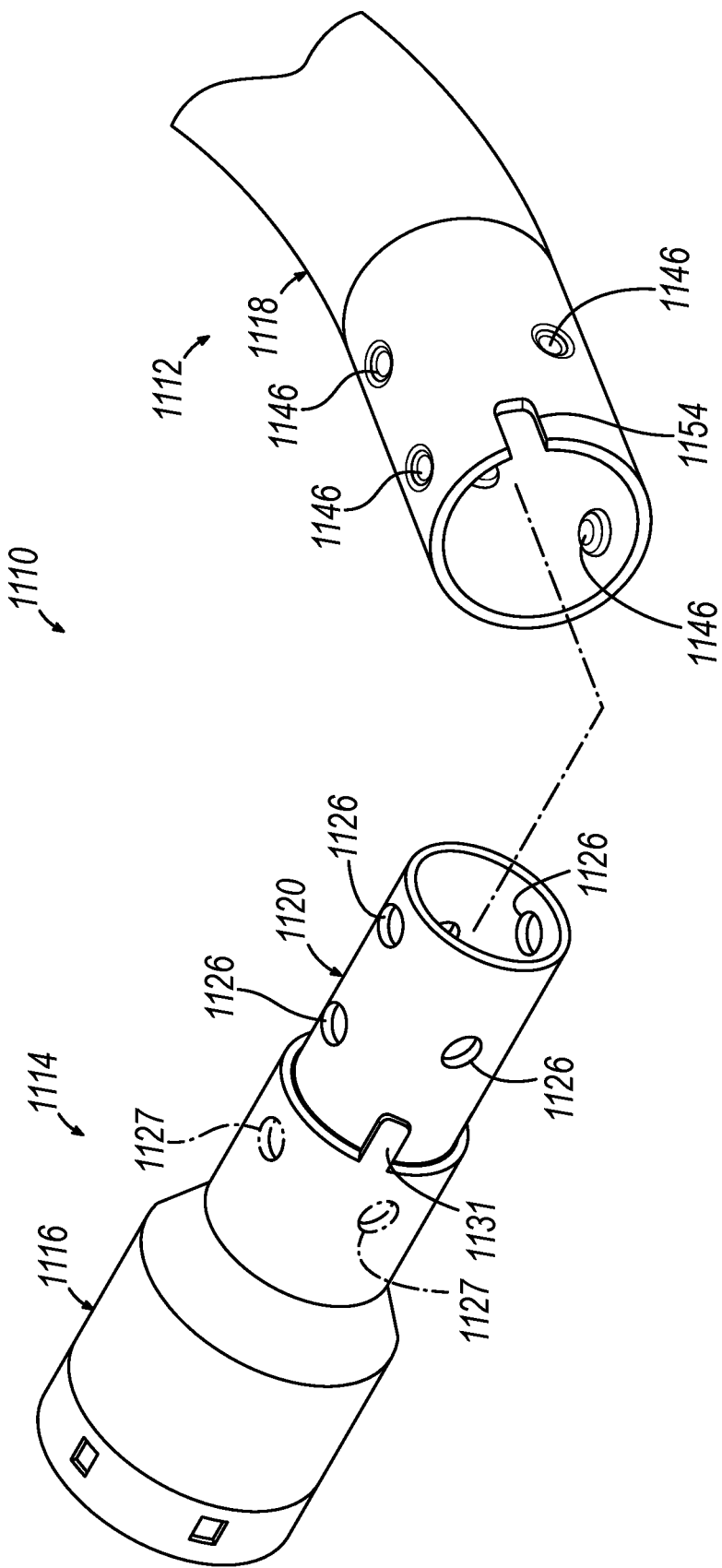
FIG. 18 depicts a partial perspective view of another exemplary circular surgical stapler that includes a shaft assembly and a stapling head assembly, with the shaft assembly and the stapling head assembly shown separated from each other, showing a rigid collar of the stapling head assembly having a plurality of bores configured to receive corresponding crimp detents of the shaft assembly.

G. Exemplary Stapling Head Assembly Overmolded onto Collar with Bores and Exemplary Shaft Assembly with Corresponding Crimp Detents FIG. 18 shows a portion of another exemplary circular surgical stapling instrument (1110) that may be used to form anastomosis (70), and including a handle assembly (not shown), such as handle assembly (100), a shaft assembly (1112) extending distally from the handle assembly, a stapling head assembly (1114) at a distal end of shaft assembly (1112), and an anvil (not shown), such as anvil (400), configured to releasably couple and cooperate with stapling head assembly (1114) to clamp, staple, and cut tissue. Shaft assembly (1112) and stapling head assembly (1114) are similar to shaft assembly (512) and stapling head assembly (514) described above, respectively, except as otherwise described below. In this regard, stapling head assembly (1114) of this example is coupled to a distal end of shaft assembly (1112) and includes a tubular body member (1116) and a staple driver member (not shown), such as staple driver member (350), slidably housed therein, and shaft assembly (1112) of this example includes an outer sheath (1118) that extends between the handle assembly and body member (1116).

In the example shown, stapling head assembly (1114) includes a proximal rigid collar (1120) separately formed from and fixedly secured to body member (1116) and including a plurality of bores (1126) extending radially through a proximal portion of collar (1120). Collar (1120) of the present version also includes a plurality of overmolding features in the form of an annular array of apertures (1127) for receiving flowable material of body member (1116) during overmolding of body member (1116) onto collar (1120). In this regard, collar (1120) may be constructed of a metallic material such as aluminum, for example. While body member (1116) of the present example is overmolded onto collar (1120), it will be appreciated that body member (1116) may be fixedly secured to collar (1120) in any other suitable manner. In any event, body member (1116) includes a proximally-extending key (1131) disposed radially outwardly of collar (1120).

In the example shown, outer sheath (1118) of shaft assembly (1112) has an internal diameter substantially equal to or slightly greater than an external diameter of collar (1120) to permit collar (1120) to be slidably received within outer sheath (1118). Outer sheath (1118) also includes a plurality of crimp detents (1146) which may initially extend radially outwardly from a radially outer surface of outer sheath (1118) for radial alignment with corresponding bores (1126) of collar (1120). Each detent (1146) may have a cross dimension substantially equal to or slightly less than that of bores (1126) of collar (1120) to permit detents (1146) to be received within corresponding bores (1126), such as via crimping of detents (1146) to extend radially inwardly from a radially inner surface of outer sheath (1118). As shown, outer sheath (1118) further includes a longitudinal keyway (1154) extending proximally from a distal end of outer sheath (1118) and configured to cooperate with key (1131) to promote proper angular alignment between shaft assembly (1112) and stapling head assembly (1114).

III. Exemplary Features for Coupling Separate Portions of Shaft Assembly

As described above, outer sheath (210) of shaft assembly (200) includes a medial portion that extends along a curved path. In some instances, the curved medial portion of outer sheath (210) may be separately formed from a straight proximal portion of outer sheath (210). It will be appreciated that such proximal and medial portions of outer sheath (210) may be fixedly secured to each other via any suitable coupling technique to inhibit inadvertent detachment of the proximal and medial portions from each other. For example, the proximal and medial portions of outer sheath (210) may be fixedly secured to each other via magneforming, such as by inducing a current in the proximal and/or medial portions using pulsed electromagnetic fields to thereby reshape a distal end of the proximal portion into secure engagement with a proximal end of the medial portion. In some instances, it may be desirable to fixedly secure the proximal and medial portions of outer sheath (210) to each other via a different coupling technique other than magneforming, such as to reduce or eliminate the need for pulsed electromagnetic fields, for example. Each of the coupling features described below provides such functionality.

A. Exemplary Straight Sheath Portion with Crimp Detents and Exemplary Curved Sheath Portion with Corresponding Bores FIG. 19 shows a portion of an exemplary circular surgical stapling instrument (1210) that may be used to form anastomosis (70), and including a handle assembly (not shown), such as handle assembly (100), a shaft assembly (1212) extending distally from the handle assembly, a stapling head assembly (not shown), such as stapling head assembly (300), and an anvil (not shown), such as anvil (400). Shaft assembly (1212) is similar to shaft assembly (200) described above, except as otherwise described below. In this regard, shaft assembly (1212) of this example includes an outer sheath (1218) that extends between the handle assembly and a body member (not shown) of the stapling head assembly.

In the example shown, outer sheath (1218) of shaft assembly (1212) includes a straight proximal sheath portion (1240) and a curved medial sheath portion (1242) separately formed from and fixedly secured to each other. In this regard, curved medial sheath portion (1242) of outer sheath (1218) includes a proximal collar (1250) extending proximally from a shoulder (1252) and including a plurality of bores (1254) extending radially through collar (1250).

Proximal sheath portion (1240) of outer sheath (1218) has an internal diameter substantially equal to or slightly greater than an external diameter of collar (1250) to permit collar (1250) to be slidably received within proximal sheath portion (1240), and substantially equal to or slightly less than an external diameter of shoulder (1252) to provide a hard stop between shoulder (1252) and a distal end of proximal sheath portion (1240). Proximal sheath portion (1240) also includes a plurality of crimp detents (1260) which may initially extend radially outwardly from a radially outer surface of proximal sheath portion (1240) for radial alignment with corresponding bores (1254) of collar (1250). Each detent (1260) may have a cross dimension substantially equal to or slightly less than that of bores (1254) of collar (1250) to permit detents (1260) to be received within corresponding bores (1254), such as via crimping of detents (1260) to extend radially inwardly from a radially inner surface of proximal sheath portion (1240). In some versions, sheath portions (1240, 1242) may be laser welded to each other along the shoulder (1252) and the distal end of proximal sheath portion (1240). In this regard, sheath portions (1240, 1242) may each be constructed of a laser weldable material such as a metallic material, for example.

Figure 21:
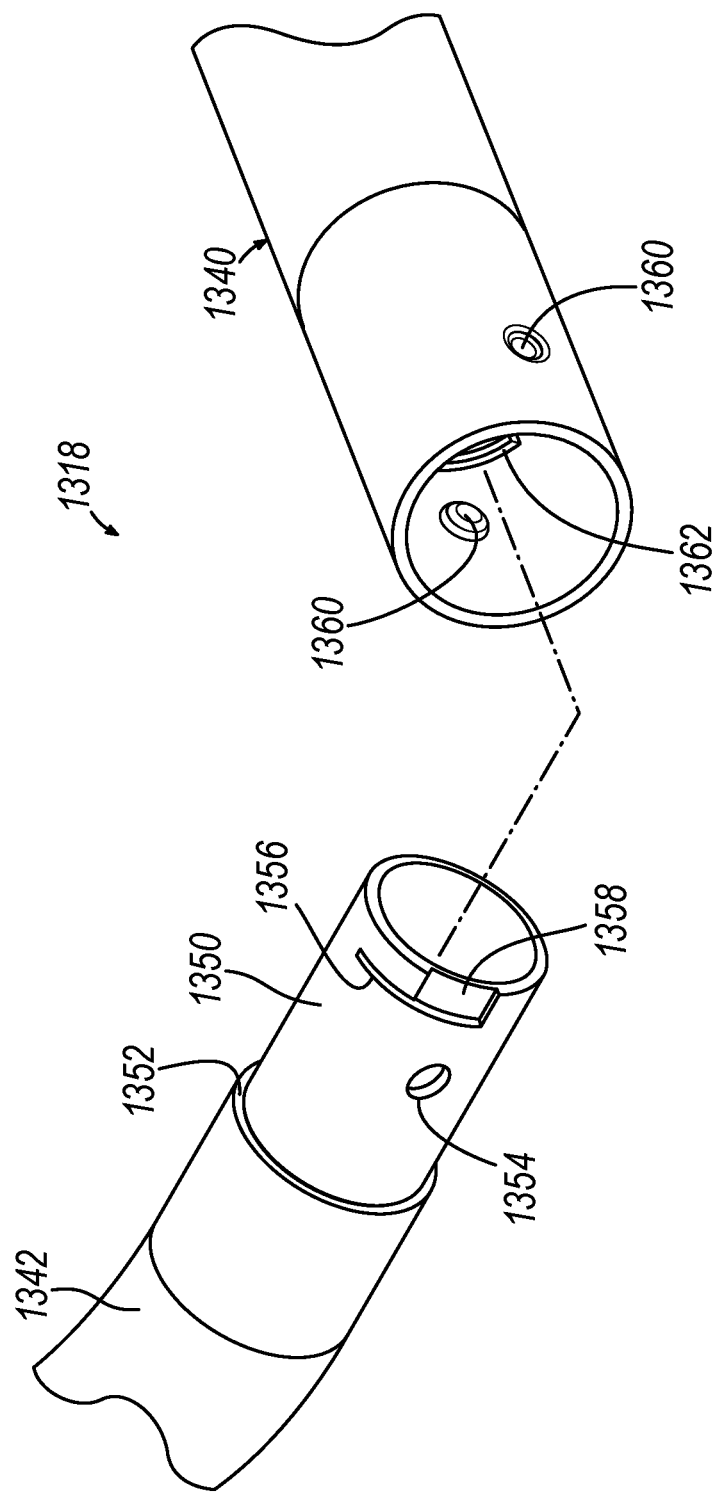
FIG. 21 depicts a partial perspective view of the circular surgical stapler of FIG. 20, with the straight and curved portions shown separated from each other.

B. Exemplary Straight Sheath Portion with Crimp Detents and Exemplary Curved Sheath Portion with Corresponding Bores and Bayonet Coupling FIGS. 20-21 show a portion of an exemplary circular surgical stapling instrument (1310) that may be used to form anastomosis (70), and including a handle assembly (not shown), such as handle assembly (100), a shaft assembly (1312) extending distally from the handle assembly, a stapling head assembly (not shown), such as stapling head assembly (300), and an anvil (not shown), such as anvil (400). Shaft assembly (1312) is similar to shaft assembly (200) described above, except as otherwise described below. In this regard, shaft assembly (1312) of this example includes an outer sheath (1318) that extends between the handle assembly and a body member (not shown) of the stapling head assembly.

In the example shown, outer sheath (1318) of shaft assembly (1312) includes a straight proximal sheath portion (1340) and a curved medial sheath portion (1342) separately formed from and fixedly secured to each other. In this regard, curved medial sheath portion (1342) of outer sheath (1318) includes a proximal collar (1350) extending proximally from a shoulder (1352) and including a laterally-opposed pair of bores (1354) (one shown) extending radially through collar (1350). Collar (1350) of the present example also includes an external semi-annular groove (1356) extending radially inwardly from a radially outer surface of collar (1350) and a proximal recessed entryway (1358) extending from a proximal end of collar (1350) to external semi-annular groove (1356), the purposes of which are described below.

Proximal sheath portion (1340) of outer sheath (1318) has an internal diameter substantially equal to or slightly greater than an external diameter of collar (1350) to permit collar (1350) to be slidably received within proximal sheath portion (1340), and substantially equal to or slightly less than an external diameter of shoulder (1352) to provide a hard stop between shoulder (1352) and a distal end of proximal sheath portion (1340). Proximal sheath portion (1340) also includes a laterally-opposed pair of crimp detents (1360) which may initially extend radially outwardly from a radially outer surface of proximal sheath portion (1340) for radial alignment with corresponding bores (1354) of collar (1350). Each detent (1360) may have a cross dimension substantially equal to or slightly less than that of bores (1354) of collar (1350) to permit detents (1360) to be received within corresponding bores (1354), such as via crimping of detents (1360) to extend radially inwardly from a radially inner surface of proximal sheath portion (1340). In the example shown, proximal sheath portion (1340) further includes an internal rib (1362) (FIG. 21) extending radially inwardly from the radially inner surface of proximal sheath portion (1340) for sliding longitudinally through recessed entryway (1358) and rotating circumferentially along external semi-annular groove (1356) of collar (1350) (e.g., by approximately 90°) to provide a bayonet-style coupling between sheath portions (1340, 1342) (e.g., prior to crimping of detents (1360)). In some versions, sheath portions (1340, 1342) may be laser welded to each other along the shoulder (1352) and the distal end of proximal sheath portion (1340). In this regard, sheath portions (1340, 1342) may each be constructed of a laser weldable material such as a metallic material, for example.

IV. Exemplary Staple Retention Features for Circular Surgical Stapler

In some instances, it may be desirable to securely retain staples (90) within the respective staple openings (324) of deck member (320) prior to performing an anastomosis procedure, such as prior to positioning anvil (400) and stapling head assembly in the respective tubular anatomical structures (20, 40). For example, it may be desirable to securely retain staples (90) within the respective staple openings (324) to inhibit inadvertent dislodgement of staples (90) from the respective staple openings (324) that might otherwise result from shock, vibrations, and/or impacts experienced by stapling head assembly (300) during transit and general handling, for example. Each of the staple retention features described below provides such functionality.

A. Exemplary Anvil Retainer for Securing Staple Retainer Between Anvil and Deck

Figure 22:
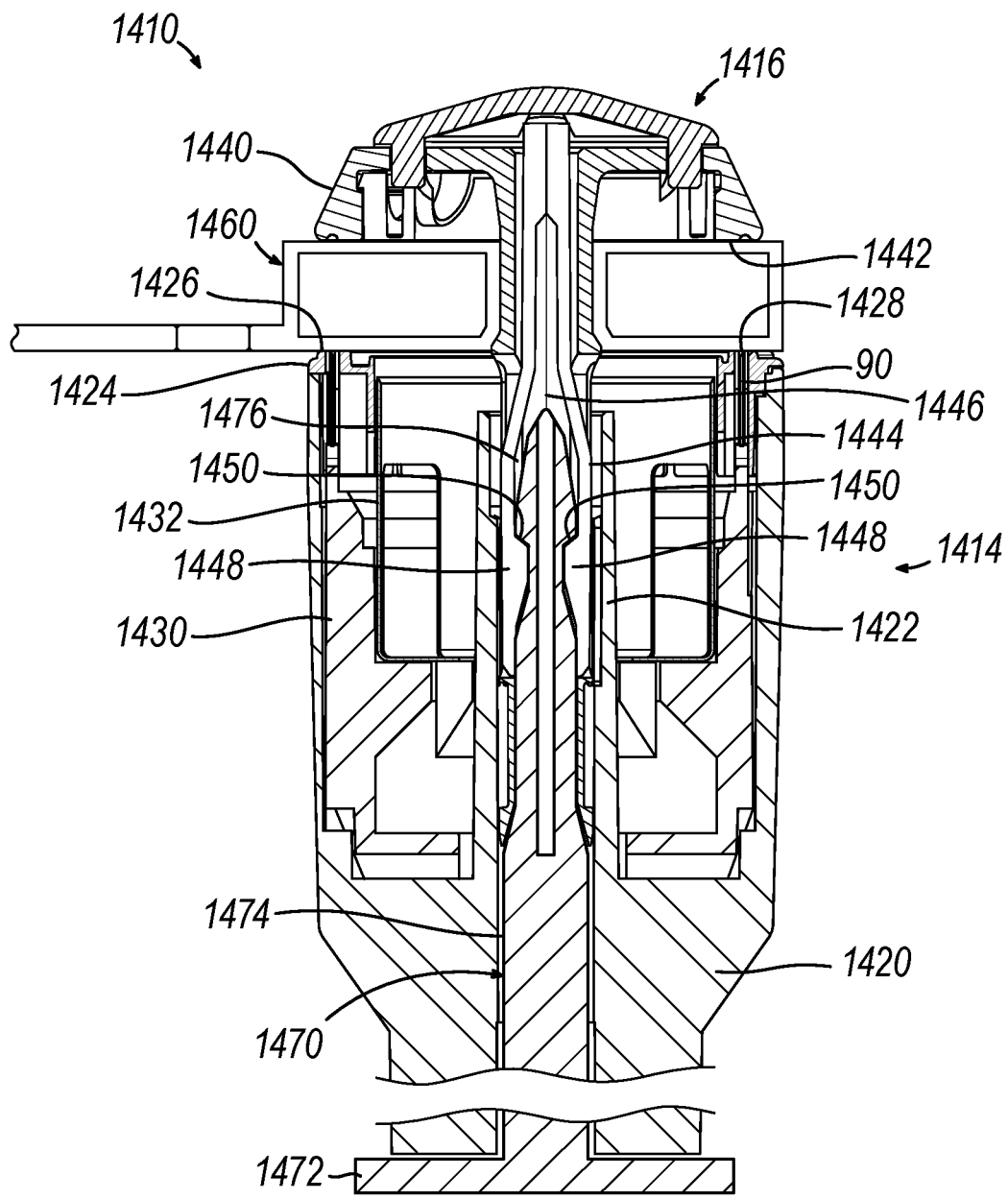
FIG. 22 depicts a cross-sectional view of an exemplary circular surgical stapler shipping assembly that includes a stapling head assembly and an anvil, showing a staple retainer sandwiched between a deck surface of the stapling head assembly and a proximal stapling surface of the anvil via an anvil retainer.

FIG. 22 shows an exemplary circular surgical stapling instrument shipping assembly (1410) including a stapling head assembly (1414) and an anvil (1416). Stapling head assembly (1414) and anvil (1416) are similar to stapling head assembly (300) and anvil (400) described above, respectively, except as otherwise described below. In this regard, stapling head assembly (1414) of this example includes a tubular body member (1420) having a distally extending cylindraceous inner core member (1422), an annular deck member (1424) fixedly secured to a distal end of body member (1420) and including a deck surface (1426) having staple openings (1428), a staple driver member (1430) slidably housed within body member (1420), and a cylindraceous knife member (1432) coaxially positioned within a distally-opening central recess of staple driver member (1430). Anvil (1416) of this example includes a head (1440) including a proximal stapling surface (1442), a shank (1444) defining a bore (1446) and including a pair of pivoting latch members (1448) with corresponding latch shelves (1450). As shown, stapling head assembly (1414) is detached from a shaft assembly (not shown) of the circular surgical stapling instrument, such as for facilitating shipping of stapling head assembly (1414) and anvil (1416) separately from the remaining components of the circular surgical stapling instrument.

In the example shown, shipping assembly (1410) also includes a staple retainer (1460) disposed between proximal stapling surface (1442) of anvil (1416) and deck surface (1426) of stapling head assembly (1414) to capture staples (90) within the respective staple openings (1428) of deck member (1424), such as during shipping. In this regard, shipping assembly (1410) further includes an anvil retainer (1470) configured to cooperate with anvil (1416) to releasably secure staple retainer (1460) against deck surface (1426). Anvil retainer (1470) of the present version includes a proximal plate (1472) and a shaft (1474) extending distally therefrom to a distal contractable head (1476). Head (1476) and a distal portion of shaft (1474) are configured for insertion into bore (1446) of anvil (1416), with head (1476) being configured to be radially contracted by latch shelves (1450) to permit distal advancement of head (1476) therebetween and to subsequently be seated against distal surfaces of latch shelves (1450). Anvil (1416) is thus secured to anvil retainer (1470) through a snap fit provided by head (1476). As shown, shaft (1474) may be sized such that a distal surface of proximal plate (1472) abuts a proximal surface of staple driver member (1430) and/or a proximal surface of body member (1420) when anvil (1416) is secured to anvil retainer (1470). In this manner, proximal plate (1472) of anvil retainer (1470) and proximal stapling surface (1442) of anvil (1416) may sandwich stapling head assembly (1414) and staple retainer (1460) therebetween, such that staple retainer (1460) may be firmly lodged between proximal stapling surface (1442) of anvil (1416) and deck surface (1426) of stapling head assembly (1414) until anvil retainer (1470) is proximally retracted from bore (1446) of anvil (1416).

In some versions, circular surgical stapling instrument shipping assembly (1410) may be shipped from a first manufacturer to a second manufacturer with staples (90) loaded within the respective staple openings (1428), and the second manufacturer may remove anvil retainer (1470) and stapler retainer (1460) prior to coupling stapling head assembly (1414) to the distal end of the shaft assembly.

B. Exemplary Staple Retainer with Integral Flexible Tabs

Figure 23:
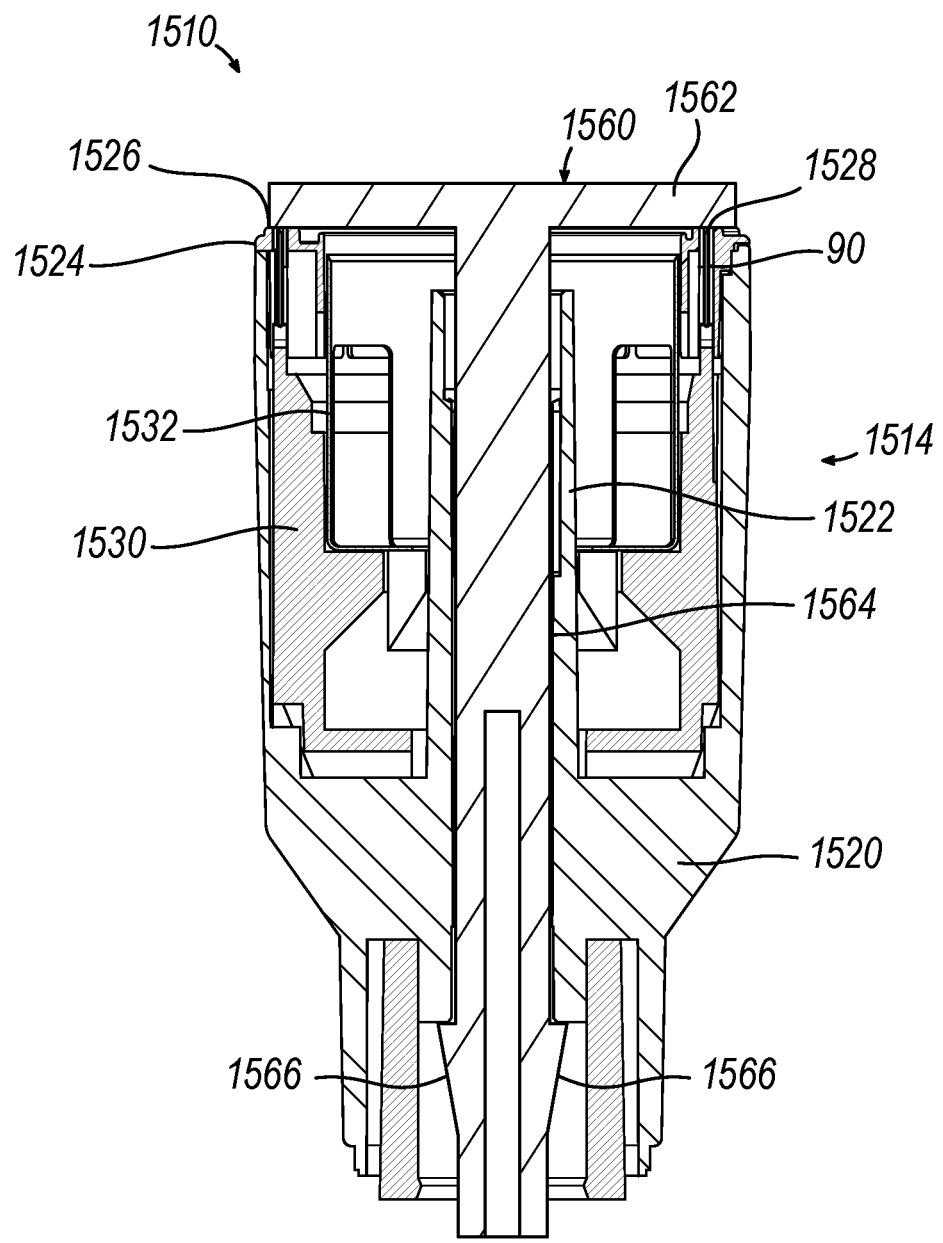
FIG. 23 depicts a cross-sectional view of an exemplary circular surgical stapler shipping assembly that includes a stapling head assembly, showing a distal plate of a staple retainer held against a deck surface of the stapling head assembly via proximal clips of the staple retainer.

FIG. 23 shows another exemplary circular surgical stapling instrument shipping assembly (1510) including a stapling head assembly (1514). Stapling head assembly (1514) is similar to stapling head assembly (300) described above, except as otherwise described below. In this regard, stapling head assembly (1514) of this example includes a tubular body member (1520) having a distally extending cylindraceous inner core member (1522), an annular deck member (1524) fixedly secured to a distal end of body member (1520) and including a deck surface (1526) having staple openings (1528), a staple driver member (1530) slidably housed within body member (1520), and a cylindraceous knife member (1532) coaxially positioned within a distally-opening central recess of staple driver member (1530). As shown, stapling head assembly (1514) is detached from a shaft assembly (not shown) of the circular surgical stapling instrument, such as for facilitating shipping of stapling head assembly (1514) separately from the remaining components of the circular surgical stapling instrument.

In the example shown, shipping assembly (1510) also includes a staple retainer (1560) having a distal plate (1562) releasably secured against deck surface (1526) of stapling head assembly (1514) to capture staples (not shown) within the respective staple openings (1528) of deck member (1524), such as during shipping. In this regard, staple retainer (1560) of the present version also includes a shaft (1564) extending proximally from distal plate (1562) to a plurality of proximal flexible clips (1566). Clips (1566) and a proximal portion of shaft (1564) are configured for insertion into inner core member (1522) of stapling head assembly (1514), with clips (1566) being configured to be radially contracted by a radially inner surface of inner core member (1522) to permit proximal advancement of clips (1566) therethrough and to subsequently be seated against a proximally-facing surface of body member (1520). Staple retainer (1560) is thus secured to stapling head assembly (1514) through a snap fit provided by clips (1566). As shown, shaft (1564) may be sized such that a proximal surface of distal plate (1562) abuts deck surface (1526) when staple retainer (1560) is secured to stapling head assembly (1514), such that staple retainer (1560) may be firmly held against deck surface (1526) of stapling head assembly (1514) until staple retainer (1560) is distally retracted from inner core member (1522) of stapling head assembly (1514).

In some versions, circular surgical stapling instrument shipping assembly (1510) may be shipped from a first manufacturer to a second manufacturer with staples (90) loaded within the respective staple openings (1528), and the second manufacturer may remove stapler retainer (1560) prior to coupling stapling head assembly (1514) to the distal end of the shaft assembly.

V. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapling instrument, comprising (a) a body member having a distal end, wherein the distal end is configured to be fixedly secured to an annular deck member having a plurality of staple openings, wherein the body member is configured to slidably house a staple driver member, wherein the body member includes a radially expandable collar having at least one latching feature; and (b) a shaft assembly, comprising (i) a proximal sheath portion, (ii) a distal sheath portion, and (iii) at least one protrusion extending radially outwardly from the distal sheath portion, wherein the at least one protrusion includes at least one abutment surface configured to engage the at least one latching feature of the radially expandable collar for coupling the body member to the shaft assembly.

Example 2

The surgical stapling instrument of Example 1, wherein the at least one protrusion includes at least one cam surface configured to engage the radially expandable collar for transitioning the radially expandable collar from a radially unexpanded state toward a radially expanded state.

Example 3

The surgical stapling instrument of Example 2, wherein the at least one cam surface is distal of the at least one abutment surface.

Example 4

The surgical stapling instrument of any one or more of Examples 1 through 3, wherein the radially expandable collar is defined by a plurality of circumferentially-arranged flexible tabs spaced apart from each other by a plurality of longitudinal slots.

Example 5

The surgical stapling instrument of Example 4, wherein the plurality of longitudinal slots includes a first longitudinal slot having a first slot width and a second longitudinal slot having a second slot width greater than the first slot width, wherein the shaft assembly further comprises a longitudinal key having a key width greater than the first slot width and less than or equal to the second slot width, wherein the longitudinal key is configured to be slidably received within the second slot.

Example 6

The surgical stapling instrument of any one or more of Examples 4 through 5, wherein the radially expandable collar includes a plurality of retention features configured to collectively receive a crimp ring.

Example 7

The surgical stapling instrument of Example 6, wherein the plurality of retention features includes an annular array of external arcuate grooves extending radially inwardly from radially outer surfaces of respective flexible tabs.

Example 8

The surgical stapling instrument of any one or more of Examples 6 through 7, further comprising the crimp ring, wherein the crimp ring is collectively received by the plurality of retention features.

Example 9

The surgical stapling instrument of any one or more of Examples 6 through 8, wherein the plurality of retention features is proximal of the at least one latching feature.

Example 10

The surgical stapling instrument of any one or more of Examples 6 through 9, wherein the shaft assembly further comprises a channel proximal of the at least one protrusion, wherein the plurality of retention features is configured to be radially aligned with the channel when the at least one abutment surface of the at least one protrusion is engaged with the at least one latching feature of the radially expandable collar.

Example 11

The surgical stapling instrument of any one or more of Examples 1 through 10, wherein the at least one latching feature includes at least one internal arcuate groove extending radially outwardly from a radially inner surface of the collar, wherein the at least one protrusion includes an annular ridge configured to be received within the at least one internal arcuate groove.

Example 12

The surgical stapling instrument of any one or more of Examples 1 through 11, wherein the at least one latching feature includes at least one aperture extending radially between radially inner and outer surfaces of the collar, wherein the at least one protrusion includes at least one detent configured to be received within the at least one aperture.

Example 13

The surgical stapling instrument of any one or more of Examples 1 through 12, wherein the proximal sheath portion is wider than the distal sheath portion to define a shoulder therebetween.

Example 14

The surgical stapling instrument of any one or more of Examples 1 through 13, further comprising an anvil defining a plurality of staple forming pockets.

Example 15

The surgical stapling instrument of any one or more of Examples 1 through 14, further comprising a stapling head assembly, wherein the body member is presented by the stapling head assembly, wherein the stapling head assembly further comprises (i) an annular deck member, wherein the annular deck member includes a plurality of staple openings, and (ii) a staple driver member slidably housed within the body member, wherein the staple driver member is configured to drive the plurality of staples from the staple openings of the deck member.

Example 16

A surgical stapling instrument, comprising (a) an anvil defining a plurality of staple forming pockets; (b) a stapling head assembly configured to drive a plurality of staples against the staple forming pockets of the anvil, wherein the stapling head assembly comprises (i) an annular deck member, wherein the annular deck member includes a plurality of staple openings, (ii) a staple driver member, wherein the staple driver member is configured to drive the plurality of staples from the staple openings of the deck member against the staple forming pockets of the anvil, and (iii) a body member fixedly secured to the annular deck member, wherein the staple driver member is slidably housed within the body member, wherein the body member includes at least one flexible tab having at least one latching feature; and (c) a shaft assembly, comprising (i) a proximal sheath portion, (ii) a distal sheath portion, and (iii) at least one protrusion extending radially outwardly from the distal sheath portion, wherein the at least one protrusion includes at least one abutment surface configured to engage the at least one latching feature of the at least one flexible tab for coupling the stapling head assembly to the shaft assembly.

Example 17

A method of manufacturing a surgical stapling instrument including (i) a body member including a collar having at least one latching feature, the body member being configured to slidably house a staple driver member, and (ii) a shaft assembly having a sheath portion and at least one protrusion extending radially outwardly from the sheath portion, the at least one protrusion including at least one abutment surface, the method comprising (a) slidably positioning the sheath portion within the collar; (b) advancing a proximal portion of the collar proximally over the at least one protrusion, wherein the act of advancing includes transitioning the collar from a radially unexpanded state to a radially expanded state; and (c) after the act of advancing, transitioning the collar from the radially expanded state toward the radially unexpanded state to engage the at least one latching feature with the at least one abutment surface for coupling the body member to the shaft assembly.

Example 18

The method of Example 17, wherein the act of advancing includes engaging at least one cam surface of the at least one protrusion with the proximal portion of the collar to transition the collar from the radially unexpanded state to the radially expanded state.

Example 19

The method of any one or more of Examples 17 through 18, further comprising angularly aligning a key of one of the body member or the shaft assembly with a keyway of the other of the body member or the shaft assembly prior to the act of advancing.

Example 20

The method of any one or more of Examples 17 through 19, further comprising positioning a crimp ring over the collar to secure the collar in the radially unexpanded state.

VI. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapling instrument, comprising:
   (a) a body member having a distal end, wherein the distal end is configured to be fixedly secured to an annular deck member having a plurality of staple openings, wherein the body member is configured to slidably house a staple driver member, wherein the body member includes a radially expandable collar having at least one latching feature; and
   (b) a shaft assembly, comprising:
      (i) a proximal sheath portion,
      (ii) a distal sheath portion, and
      (iii) at least one protrusion extending radially outwardly from the distal sheath portion, wherein the at least one protrusion includes at least one abutment surface configured to engage the at least one latching feature of the radially expandable collar for coupling the body member to the shaft assembly.

2. The surgical stapling instrument of claim 1, wherein the at least one protrusion includes at least one cam surface configured to engage the radially expandable collar for transitioning the radially expandable collar from a radially unexpanded state toward a radially expanded state.

3. The surgical stapling instrument of claim 2, wherein the at least one cam surface is distal of the at least one abutment surface.

4. The surgical stapling instrument of claim 1, wherein the radially expandable collar is defined by a plurality of circumferentially-arranged flexible tabs spaced apart from each other by a plurality of longitudinal slots.

5. The surgical stapling instrument of claim 4, wherein the plurality of longitudinal slots includes a first longitudinal slot having a first slot width and a second longitudinal slot having a second slot width greater than the first slot width, wherein the shaft assembly further comprises a longitudinal key having a key width greater than the first slot width and less than or equal to the second slot width, wherein the longitudinal key is configured to be slidably received within the second slot.

6. The surgical stapling instrument of claim 4, wherein the radially expandable collar includes a plurality of retention features configured to collectively receive a crimp ring.

7. The surgical stapling instrument of claim 6, wherein the plurality of retention features includes an annular array of external arcuate grooves extending radially inwardly from radially outer surfaces of respective flexible tabs.

8. The surgical stapling instrument of claim 6, further comprising the crimp ring, wherein the crimp ring is collectively received by the plurality of retention features.

9. The surgical stapling instrument of claim 6, wherein the plurality of retention features is proximal of the at least one latching feature.

10. The surgical stapling instrument of claim 6, wherein the shaft assembly further comprises a channel proximal of the at least one protrusion, wherein the plurality of retention features is configured to be radially aligned with the channel when the at least one abutment surface of the at least one protrusion is engaged with the at least one latching feature of the radially expandable collar.

11. The surgical stapling instrument of claim 1, wherein the at least one latching feature includes at least one internal arcuate groove extending radially outwardly from a radially inner surface of the collar, wherein the at least one protrusion includes an annular ridge configured to be received within the at least one internal arcuate groove.

12. The surgical stapling instrument of claim 1, wherein the at least one latching feature includes at least one aperture extending radially between radially inner and outer surfaces of the collar, wherein the at least one protrusion includes at least one detent configured to be received within the at least one aperture.

13. The surgical stapling instrument of claim 1, wherein the proximal sheath portion is wider than the distal sheath portion to define a shoulder therebetween.

14. The surgical stapling instrument of claim 1, further comprising an anvil defining a plurality of staple forming pockets.

15. The surgical stapling instrument of claim 1, further comprising a stapling head assembly, wherein the body member is presented by the stapling head assembly, wherein the stapling head assembly further comprises:
   (i) an annular deck member, wherein the annular deck member includes a plurality of staple openings, and
   (ii) a staple driver member slidably housed within the body member, wherein the staple driver member is configured to drive the plurality of staples from the staple openings of the deck member.

16. A surgical stapling instrument, comprising:
(a) an anvil defining a plurality of staple forming pockets;
(b) a stapling head assembly configured to drive a plurality of staples against the staple forming pockets of the anvil, wherein the stapling head assembly comprises:
  (i) an annular deck member, wherein the annular deck member includes a plurality of staple openings,
  (ii) a staple driver member, wherein the staple driver member is configured to drive the plurality of staples from the staple openings of the deck member against the staple forming pockets of the anvil, and
  (iii) a body member fixedly secured to the annular deck member, wherein the staple driver member is slidably housed within the body member, wherein the body member includes a radially expandable collar having at least one latching feature; and
(c) a shaft assembly, comprising:
  (i) a proximal sheath portion,
  (ii) a distal sheath portion, and
  (iii) at least one protrusion extending radially outwardly from the distal sheath portion, wherein the at least one protrusion includes at least one abutment surface configured to engage the at least one latching feature of the radially expandable collar for coupling the stapling head assembly to the shaft assembly.

17. A method of manufacturing a surgical stapling instrument including (i) a body member including a collar having at least one latching feature, the body member being configured to slidably house a staple driver member, and (ii) a shaft assembly having a sheath portion and at least one protrusion extending radially outwardly from the sheath portion, the at least one protrusion including at least one abutment surface, the method comprising:
(a) slidably positioning the sheath portion within the collar;
(b) advancing a proximal portion of the collar proximally over the at least one protrusion, wherein the act of advancing includes transitioning the collar from a radially unexpanded state to a radially expanded state; and
(c) after the act of advancing, transitioning the collar from the radially expanded state toward the radially unexpanded state to engage the at least one latching feature with the at least one abutment surface for coupling the body member to the shaft assembly.

18. The method of claim 17, wherein the act of advancing includes engaging at least one cam surface of the at least one protrusion with the proximal portion of the collar to transition the collar from the radially unexpanded state to the radially expanded state.

19. The method of claim 17, further comprising angularly aligning a key of one of the body member or the shaft assembly with a keyway of the other of the body member or the shaft assembly prior to the act of advancing.

20. The method of claim 17, further comprising positioning a crimp ring over the collar to secure the collar in the radially unexpanded state.

* * * * *